(12) United States Patent
Shigemori

(10) Patent No.: US 6,808,885 B2
(45) Date of Patent: Oct. 26, 2004

(54) TRIPLE-STRANDED DNA, METHOD OF FORMING THE SAME AND SOUTHERN HYBRIDIZATION

(75) Inventor: Yasushi Shigemori, Kisarazu (JP)

(73) Assignee: Aisin Seiki Kabushiki Kaisha, Kariya (JP)

(*) Notice: Subject to any disclaimer, the term of this patent is extended or adjusted under 35 U.S.C. 154(b) by 91 days.

(21) Appl. No.: 10/101,938

(22) Filed: Mar. 21, 2002

(65) Prior Publication Data
US 2003/0044819 A1 Mar. 6, 2003

(30) Foreign Application Priority Data

Mar. 21, 2001 (JP) ........................................ 2001-081527

(51) Int. Cl.$^7$ ............................ C12Q 1/68; C12Q 1/44; C12Q 1/37
(52) U.S. Cl. ................ 435/6; 435/19; 435/23
(58) Field of Search .................... 435/6, 68.1, 69.1, 435/23, 19, 91.42, 91.1, 91.53; 536/23.1

(56) References Cited

U.S. PATENT DOCUMENTS

| | | | |
|---|---|---|---|
| 6,090,918 A | * | 7/2000 | Parnet et al. ............... 530/350 |
| 6,114,121 A | | 9/2000 | Fujiwara et al. ............... 435/6 |
| 6,132,972 A | * | 10/2000 | Shigemori et al. ............. 435/6 |
| 6,541,226 B1 | * | 4/2003 | Shigemori et al. ....... 435/91.42 |

FOREIGN PATENT DOCUMENTS

| WO | WO 87/01730 | * | 3/1987 |
|---|---|---|---|

OTHER PUBLICATIONS

Rao et al. Stable three-stranded DNA made by RecA protein. Proc. Natl. Acad. Sci. USA, vol. 88, pp. 2984–2988, Apr. 1991.*

Mahdi et al. DNA binding and helicase domains of the E. coli recombination protein recG. Nucleic acids research. Vol. 25, No. 19, pp. 3875–3880, Oct. 1997.*

B. Jagadeeshwar Rao et al., Proc. Natl. Acad. Sci. USA, 88, 2984–2988(1991).

Gurucharan Reddy et al., Biochemistry, 33, 11486–11492 (1994).

Effim I. Golub et al., Mutation Research, 351, 117–124 (1996).

* cited by examiner

Primary Examiner—Kenneth R. Horlick
Assistant Examiner—Cynthia Wilder
(74) Attorney, Agent, or Firm—Oblon, Spivak, McClelland, Maier & Neustadt, P.C.

(57) ABSTRACT

The present invention provides methods of preparing a triple-stranded DNA molecule by forming a DNA and protein complex, which DNA has a linear double-stand molecule and a single-strand molecule where the linear single-stranded DNA is complementary to a 5' end region of one strand in the linear double stranded DNA; and the protein component is a homogeneous recombinant protein and an exonuclease; and then the protein is removed from the complex; triple-stranded DNA; and methods of using the triple-stranded DNA to detect nucleic acid sequence.

10 Claims, 19 Drawing Sheets

Fig.1
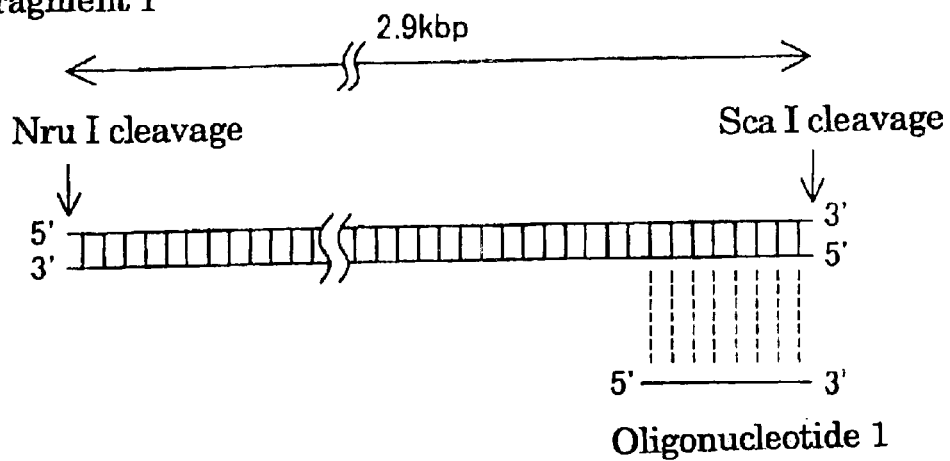
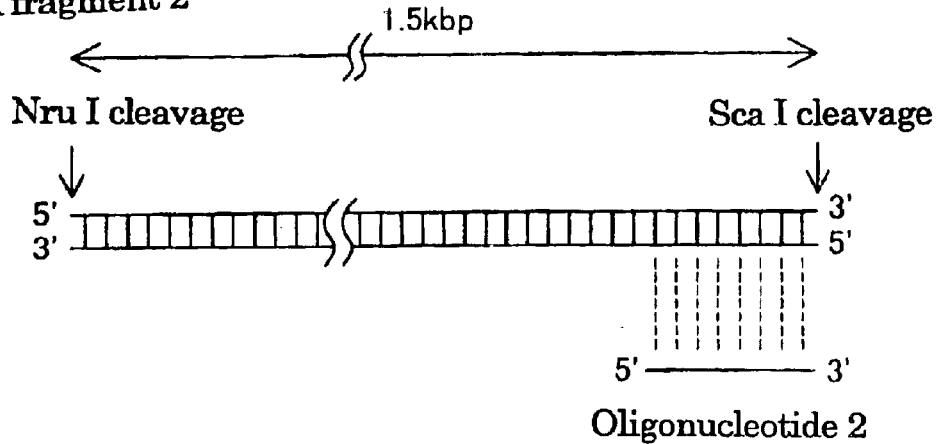

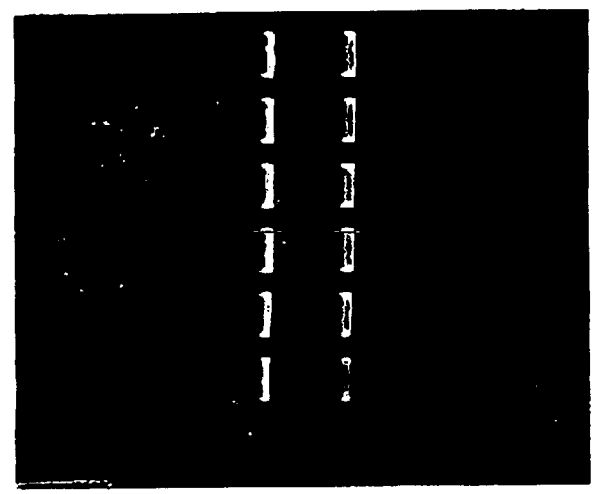
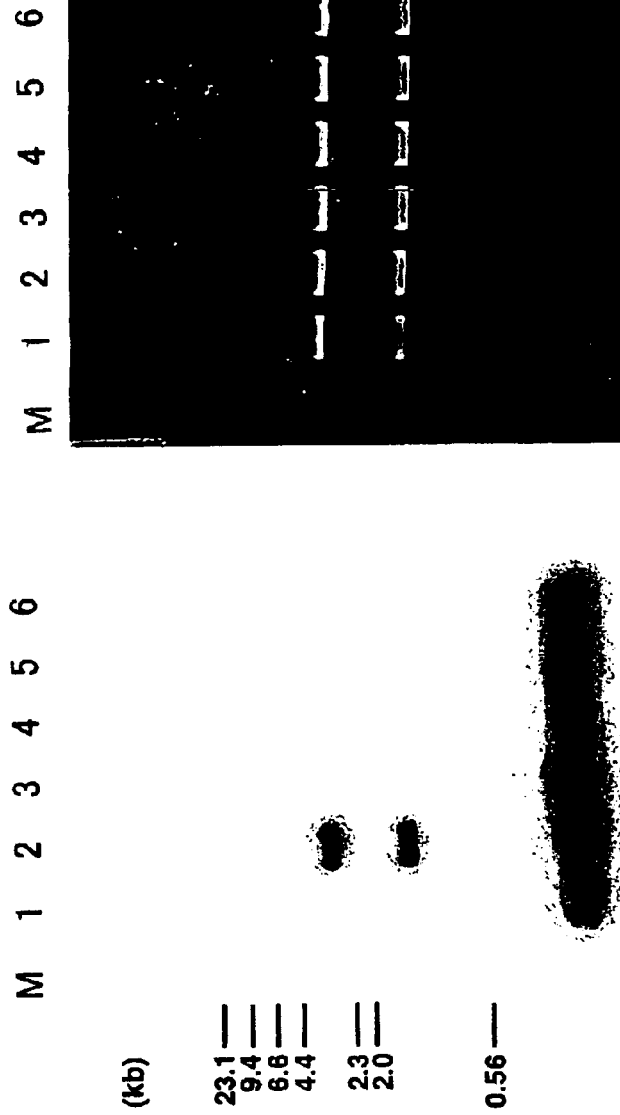
FIG.3A / FIG.3B
1: Mug Bean nuclease
2: Exonuclease I
3: Exonuclease III
4: T4 PNK
5: T4 DNA Ligase
6: None 1: Oligonucleotide 3
2: Oligonucleotide 5
3: Oligonucleotide 4
4: Oligonucleotide 6

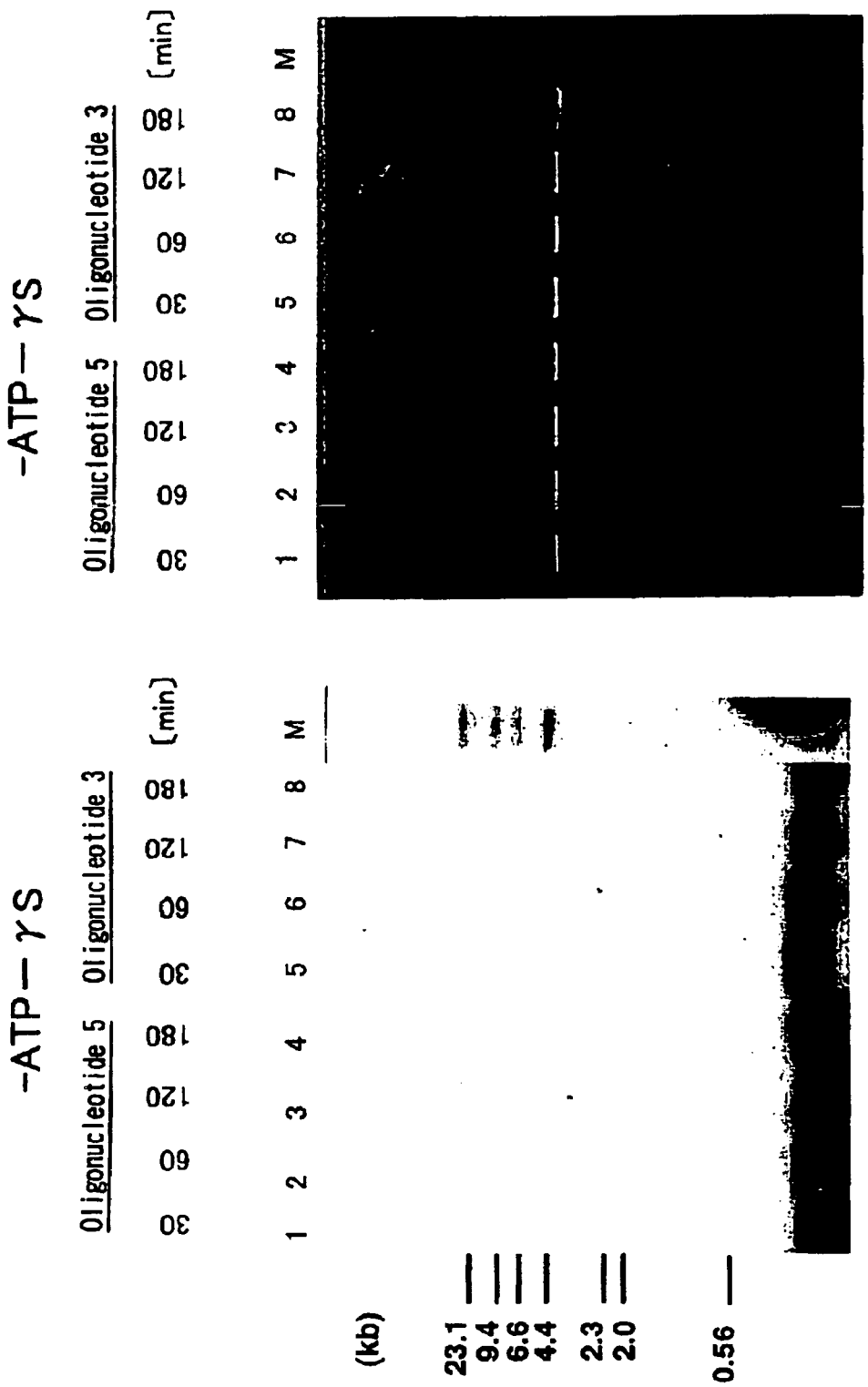

FIG.10A          ## FIG.10B
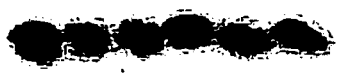
1: Oligonucleotide 3
2: Oligonucleotide 4
3: Later addition of Oligonucleotide 3
4: Later addition of Oligonucleotide 5
5: Later addition of Oligonucleotide 4
6: Later addition of Oligonucleotide 6
7: No addition of Exonuclease I
   & Later addition of Oligonucleotide 3
8: No addition of Exonuclease I
   & Later addition of Oligonucleotide 4

1: Oligonucleotide 7
2: Oligonucleotide 8
3: Oligonucleotide 9
4: Oligonucleotide 10
5: Oligonucleotide 11
6: Oligonucleotide 12
7: Oligonucleotide 13

1: Oligonucleotide 8
2: Oligonucleotide 14
3: Oligonucleotide 15
4: Oligonucleotide 16

1. Mg 0mM
2. Mg 20mM
3. Mg 40mM
4. Mg 60mM

SEQUENCE LISTING

<160> NUMBER OF SEQ ID NOS: 18

<210> SEQ ID NO 1
<211> LENGTH: 60
<212> TYPE: DNA
<213> ORGANISM: Artificial Sequence
<220> FEATURE:
<223> OTHER INFORMATION: synthetic DNA

<400> SEQUENCE: 1
cactgcataa ttctcttact gtcatgccat ccgtaagatg cttttctgtg actggtgagt    60

<210> SEQ ID NO 2
<211> LENGTH: 60
<212> TYPE: DNA
<213> ORGANISM: Artificial Sequence
<220> FEATURE:
<223> OTHER INFORMATION: synthetic DNA

<400> SEQUENCE: 2
acgccgggca agagcaactc ggtcgccgca tacactattc tcagaatgac ttggttgagt    60

<210> SEQ ID NO 3
<211> LENGTH: 60
<212> TYPE: DNA
<213> ORGANISM: Artificial Sequence

```
<220> FEATURE:
<223> OTHER INFORMATION: synthetic DNA

<400> SEQUENCE: 3
cgacgttgta aaacgacggc cagtgaattc gagctcggta cccggggatc ctctagagtc    60

<210> SEQ ID NO 4
<211> LENGTH: 60
<212> TYPE: DNA
<213> ORGANISM: Artificial Sequence
<220> FEATURE:
<223> OTHER INFORMATION: synthetic DNA

<400> SEQUENCE: 4
caatttcaca caggaaacag ctatgaccat gattacgcca agcttgcatg cctgcaggtc    60

<210> SEQ ID NO 5
<211> LENGTH: 60
<212> TYPE: DNA
<213> ORGANISM: Artificial Sequence
<220> FEATURE:
<223> OTHER INFORMATION: synthetic DNA

<400> SEQUENCE: 5
gactctagag gatccccggg taccgagctc gaattcactg gccgtcgttt tacaacgtcg    60

<210> SEQ ID NO 6
<211> LENGTH: 60
<212> TYPE: DNA
<213> ORGANISM: Artificial Sequence
<220> FEATURE:
<223> OTHER INFORMATION: synthetic DNA

<400> SEQUENCE: 6
gacctgcagg catgcaagct tggcgtaatc atggtcatag ctgtttcctg tgtgaaattg    60

<210> SEQ ID NO 7
<211> LENGTH: 80
<212> TYPE: DNA
<213> ORGANISM: Artificial Sequence
<220> FEATURE:
<223> OTHER INFORMATION: synthetic DNA

<400> SEQUENCE: 7
acgagggtag caacggctac agaggctttg aggactaaag acttttttcat gaggaagttt    60 ccattaaacg ggtaaaatac                                                 80

<210> SEQ ID NO 8
<211> LENGTH: 60
<212> TYPE: DNA
<213> ORGANISM: Artificial Sequence
<220> FEATURE:
<223> OTHER INFORMATION: synthetic DNA

<400> SEQUENCE: 8
agagggcttt gaggactaaa gacttttcat gaggaagttt ccattaaacg ggtaaaatac    60

<210> SEQ ID NO 9
<211> LENGTH: 50
<212> TYPE: DNA
<213> ORGANISM: Artificial Sequence
<220> FEATURE:
<223> OTHER INFORMATION: synthetic DNA

<400> SEQUENCE: 9
aggactaaag acttttttcat gaggaagttt ccattaaacg ggtaaaatac                50
```

```
<210> SEQ ID NO 10
<211> LENGTH: 40
<212> TYPE: DNA
<213> ORGANISM: Artificial Sequence
<220> FEATURE:
<223> OTHER INFORMATION: synthetic DNA

<400> SEQUENCE: 10 acttttcat gaggaagttt ccattaaacg ggtaaaatac                    40

<210> SEQ ID NO 11
<211> LENGTH: 30
<212> TYPE: DNA
<213> ORGANISM: Artificial Sequence
<220> FEATURE:
<223> OTHER INFORMATION: synthetic DNA

<400> SEQUENCE: 11
gaggaagttt ccattaaacg ggtaaaatac                              30

<210> SEQ ID NO 12
<211> LENGTH: 20
<212> TYPE: DNA
<213> ORGANISM: Artificial Sequence
<220> FEATURE:
<223> OTHER INFORMATION: synthetic DNA

<400> SEQUENCE: 12
ccattaaacg ggtaaaatac                                         20

<210> SEQ ID NO 13
<211> LENGTH: 10
<212> TYPE: DNA
<213> ORGANISM: Artificial Sequence
<220> FEATURE:
<223> OTHER INFORMATION: synthetic DNA

<400> SEQUENCE: 13
ggtaaaatac                                                    10

<210> SEQ ID NO 14
<211> LENGTH: 60
<212> TYPE: DNA
<213> ORGANISM: Artificial Sequence
<220> FEATURE:
<223> OTHER INFORMATION: synthetic DNA

<400> SEQUENCE: 14
caacggctac agaggctttg aggactaaag acttttcat gaggaagttt ccattaaacg     60

<210> SEQ ID NO 15
<211> LENGTH: 60
<212> TYPE: DNA
<213> ORGANISM: Artificial Sequence
<220> FEATURE:
<223> OTHER INFORMATION: synthetic DNA

<400> SEQUENCE: 15
acgagggtag caacggctac agaggctttg aggactaaag acttttcat gaggaagttt     60

<210> SEQ ID NO 16
<211> LENGTH: 60
<212> TYPE: DNA
<213> ORGANISM: Artificial Sequence
<220> FEATURE:
```

-continued

```
<223> OTHER INFORMATION: synthetic DNA

<400> SEQUENCE: 16
cagcatcgga acgagggtag caacggctac agaggctttg aggactaaag acttttcat        60

<210> SEQ ID NO 17
<211> LENGTH: 60
<212> TYPE: DNA
<213> ORGANISM: Artificial Sequence
<220> FEATURE:
<223> OTHER INFORMATION: synthetic DNA

<400> SEQUENCE: 17
ctttgcagtg aaaggaatca aagaaatgga gccgtgtatc aggtggggaa gggtgggggc        60

<210> SEQ ID NO 18
<211> LENGTH: 60
<212> TYPE: DNA
<213> ORGANISM: Artificial Sequence
<220> FEATURE:
<223> OTHER INFORMATION: synthetic DNA

<400> SEQUENCE: 18
ctgtgggttg attccacacc cccgcccggc acccgcgtcc gcgccatggc catctacaag        60
```

TRIPLE-STRANDED DNA, METHOD OF FORMING THE SAME AND SOUTHERN HYBRIDIZATION

BACKGROUND OF THE INVENTION

1. Field of the Invention

The present invention is generally directed to a triple-stranded DNA, a method of forming the same, and Southern hybridization employing the same.

2. Discussion of the Background

Conventional methods are known to form a complex including double-stranded and single-stranded DNAs. That is to say, as shown in FIG. 19, a target DNA (i.e. a double-stranded DNA) and a probe DNA (i.e. a single-stranded DNA) are prepared. The probe DNA (i.e. the single-stranded DNA) has a base sequence which is substantially complementary to a portion of a base sequence of one of DNA-chains of the target DNA. These DNAs and a RecA of Escherichia coli are mixed into a solution which includes a buffer etc and the resultant mixture is held at a predetermined temperature for a sufficient time duration.

Then, a DNA-protein complex is obtained which is made up of the target DNA, the probe DNA, and the RecA protein. In detail, first of all, the RecA protein is bound to the probe DNA to form a probe DNA-RecA protein complex. Subsequently, the resultant complex or the probe DNA-RecA protein complex is bound to the target DNA to form a DNA-protein complex which includes a three-chain formation region. At this stage, the probe DNA is believed to bind to a region of the target DNA which has a base sequence complementary to the probe DNA. The DNA-protein complex at this state, though it has the three-chain formation region, is relatively stable (see B. Jagadeeshwar Rao et al., Proc. Natl. Sci. USA, 88,2984–2988 (1991), Gurucharan Reddy at al., Biochemistry, 33,11486–11492 (1994), and Efim I. Golumb eat al., Mutation Research, 351, 117–124 (1996)).

However, as shown in FIG. 19, if the RecA protein is deactivated in such a manner that the DNA-protein complex is mixed with a sodium dodecyl sulfate (SDS) and/or a protein splitting enzyme (e.g. protease K) and the resultant mix is held at a temperature for a sufficient time duration, the bonding between the target DNA and the probe DNA dissociates in addition to a deleting the RecA protein from the DNA-protein complex. That is to say, the structure of the DNA-protein is stable by the presence of RecA protein and without RecA protein it is impossible to form or produce a triple-stranded DNA.

Therefore, in the field of biogenetics or the like, if one requires or wishes to use a triple-strained DNA, there are many restrictions as long as the triple-stranded DNA must remain in a complex with RecA Thus, a need exists to develop a method of forming a RecA protein free triple-stranded DNA whose structure remains stable.

SUMMARY OF THE INVENTION

Accordingly in order to meet the above need, the present invention provides a triple-stranded DNA whose structure can remain stable even if no protein is contained in its complex, a method of forming such a triple stranded DNA, and Southern hybridization employing such a triple-stranded DNA.

A first aspect of the present invention is to provide a method for forming a three-stranded DNA which comprises the steps of:

(a) DNA-protein complex forming process for forming a DNA-protein complex, wherein (1) a linearized double-stranded DNA, (2) a linearized single-stranded DNA including a base sequence, the base sequence being substantially complementary to a base sequence which extends from a base near 5'-end of one of DNA chains of the double-stranded DNAs, (3) a recombinant protein which is at least one of a homologous protein and another protein which is similar thereto in function, and (4) a nuclease which is at least one of an Exonuclease I of Escherichia coli and another protein which is similar thereto in function are reacted in order that in the DNA-protein complex an end neighboring inclusion region including the 5'-end of one of the DNA-chains of the double-stranded DNAs is bound to a complementary region including the substantially complementary base sequence of the single-stranded DNA under a participation of at least the recombinant protein; and (b) protein deactivating process deactivating both the recombinant protein and nuclease to bind the complementary region of the single-stranded DNA to the end neighboring inclusion region of the double-stranded DNA.

In accordance with the first aspect of the present invention in the DNA-protein complex forming process, the DNA-protein complex is formed from the double-stranded DNA, the recombinant protein, and the nuclease. Thereafter, in the subsequent protein deactivating process, deactivating the recombinant protein and the nuclease makes it possible to form the triple-stranded DNA which has the 3-chain forming region which is formed by the bonding between the end neighboring inclusion region of the double-stranded DNA and the complementary region of the single-stranded DNA. Thus-formed triple-stranded DNA can remain its structure i.e. cannot be disassociated, even if a heat is applied thereto more or less, without having to pare a specially prepared protein such as RecA for stabilizing the structure. It is to be noted that the present invention makes it possible to form the 3-chain forming region on both of the end neighboring inclusion regions of the double-stranded DNA other than the formation on one of the end neighboring inclusion regions.

The above-mentioned method for forming a triple-stranded DNA is applicable to, say, southern hybridization.

In the conventional southern hybridization, the operations, for example, are as follows. As a target DNA a restriction-enzymatically cleaved linearized double-stranded DNA is prepared, while as a probe DNA a single-stranded DNA is prepared whose 5'-end is labeled with 32P with usage of T4 Polynucleotide kinase and [γ-32P]. The target DNA (i.e. the double-stranded DNA) is subjected to agarose gel electrophoresis and the agarose gel is placed on a membrane for vacuum filtration or the like and the target DNA (i.e. the double-stranded DNA) in the agarose gel is transfer onto the membrane. Thereafter, the target DNA (i.e. the double-stranded DNA) is made into a single-stranded state by disassociation as well as the resulting target DNA (i.e. the double-stranded DNA) is made immobilized on the membrane. Then, the resulting membrane is immersed into a solution of the probe DNA (i.e. a solution of the labeled single-stranded DNA) for hybridization and the membrane is made cleaned. Thereafter, the membrane is taken with a picture of autoradiogram to record a signal on an X-ray film which results from the labeled probe, DNA (i.e., the labeled single-stranded DNA).

On the other hand, a southern hybridization which depends on the present invention can be performed, for example, according to the following steps. In detail, like the conventional southern hybridization, a target DNA (i.e. a double-stranded DNA) and a labeled probe DNA (i.e. a labeled single-stranded DNA) are prepared At this stage, if the present invention is employed to do southern hybridization, a DNA-protein complex is formed by reacting such DNAs, a recombinant protein, and a nuclease (DNA-protein complex forming process). Thereafter, the recombinant protein and the nuclease are made deactivated to form a stable triple-stranded DNA having a 3-chain forming region (Protein deactivating process). Next, the resulting triple-stranded DNA is subject to agarose gel electrophoresis. Thereafter, the agarose gel is placed on filter paper to dry with drying device. The resulting gel is taken with a picture of autoradiogram to record a signal on an X-ray film which results from the labeled probe DNA (i.e. the labeled single-stranded DNA).

Thus-performed southern hybridization according to the present invention can be of less time operation and less cumbersome, when compared to the conventional southern hybridization. The reason is that southern hybridization according to the present invention eliminates skilled and/or long-time required operations such as transfer of DNA in agarose gel on membrane, immersing such membrane into probe DNA solution, and membrane cleaning. It is to be noted that the above description can be applied when a single-stranded DNA is used which is labeled chemically with e.g. a fluorescent material or phosphors.

At this stage, so long as in the triple-stranded DNA the 3-chain forming region is formed by chemical bonding between one of the end neighboring inclusion regions of the double-stranded DNA and the complementary region of the single-stranded DNA, the mode of such the chemical bonding is out of concern. That is to say, it is not necessary to find, between the double-stranded DNA and the single-stranded DNA, a specific chemical bonding mode such as Watson-Click type base pair or Hoogstein type base sequence. It is enough to find any mutual reaction between the double-stranded DNA and the single-stranded DNA which results in formation of a triple-stranded DNA.

Any double-stranded DNA is available so long as it is linearized. That is to say, the base sequence is out of concern and its upper limit of the chain length is not limited. Thus, or example, a huge DNA having a 3000 Mbp is available which is similar to that of human gene. Of course, the derivation of the double-stranded DNA is out of question. Thus, it is possible to use, for example, the following DNAs:
DNA derived from each of virus microbe, plant, and animal genes;
DNA obtained by reforming the above-mentioned DNA, plasmid DNA included in microbe;
chimeric DNA obtained by inserting a heterologous DNA fragment into plasmid DNA; and artificially synthesized oligonucleotide.

Any single-stranded DNA is available so long as it is a linearized DNA which includes a base sequence which is substantially complementary to a base sequence which begins at a near portion of the 5'-end of one of the DNA chains of the double-stranded DNA. That is to say, so long as this condition is satisfied, the base sequence of the single-stranded DNA is out of concern. Like the double-stranded DNA, wit respect to the single-stranded DNA no upper limit of the DNA chain exists in theory and the derivation is out of question.

The above-mentioned substantial complementary will be about 70–80% or above, preferably 100%. The reason is that as the substantial complementary becomes higher the stability of the 3-chain forming region (i.e. the triple-stranded DNA) also becomes higher. However, depending on the length of the complementary region, the degree of complementarily will vary. In addition, it may be sometimes impossible to put a case and another case in the same class, the former class being of an even complementary (e.g. 70%) throughout the complementary region, the latter being of uneven distribution of a higher complementary zone (e.g. 9%) a lower zone complementary zone (e.g. 40%).

The single-stranded DNAs include a contemporary region, resulting in the entire single-stranded DNA complexing with the double-stranded DNA or the single-stranded DNA may also include another region that does not complex with the double-stranded DNA. However, the former is preferred from viewpoint of making forming a more stable triple-stranded DNA. It is to be noted that the reason for including a base sequence which is substantially complementary to a base sequence which begins at a near portion of the end of one of the DNA chains of the double-stranded DNA is as follows: If the single-stranded DNA is complementary to only a portion (e.g. a central-positioned base sequence) other than the base sequence which begins at a near portion of the end of one of the DNA chains of the double-stranded DNA, indeed it is possible to form a stable DNA-protein complex in the DNA-protein complex forming process, however deactivating the protein in the protein deactivating process causes the double-stranded DNA and the single-stranded DNA to disassociate, thereby failing to form or produce a stable triple-stranded DNA.

Similarly, the reason for including a base sequence which is substantially complementary to a base sequence which begins at a near portion of the 5'-end of one of the DNA chains of the double-stranded DNA is as follows: If the single-stranded DNA is complementary to only a base sequence which begins at a near portion of the 3'-end of one of the DNA chains of the double-stranded DNA, indeed it is possible to form a stable DNA-protein complex in the DNA-protein complex forming process, however deactivating the protein in the protein deactivating process causes to disassociate the double-stranded DNA and the single-stranded DNA, thereby failing to form or produce a stable triple-stranded DNA.

Any recombinant protein is available so long as it is a homogeneous recombinant protein or an analog thereof(i.e. a substance whose function is similar to homogeneous recombinant protein) and enables the formation of stable complex of the triple-stranded DNAs. Examples include: RecA protein derived from *Escherichia coli, Thermus thermophilus,* Other multi-functional proteins coded by RecA gene in intestinal bacteria, RecA-like protein derived from one of *Agrobacterium tumefaciens, Bacillus subtilis, Methylophilus methylotrophus, Vibrio cholerae,* and *Ustilago maydis.* The RecA-like includes also *Saccharomyces cerevisiae* and human genes.

A reformed protein which is produced by reforming one of these proteins is available so long as the reformed protein has a function similar to that of the latter protein. An example of the reformed protein is one which is a gene product produced or derived from a gene encoding homogeneous recombinant protein by e.g. site directed mutagenesis, which includes an amino acid sequence in which one or more amino acids are made deficient, replaced, or added, and which is similar, in function, to the homogeneous recombinant protein. In addition, a protein fragment of RecA protein (i.e. RecA fragment) which is of similar function to the homogeneous recombinant protein may be used.

Any nuclease may be used and can be chosen from Exonuclease I, preferably obtained from *Escherichia coli,* or a protein which is functional similar thereto. As the latter, an Exonuclease-I-like protein is available which is derived from, for example, eucaryotic organism (eucaryotic plant and/or animal) and other Exonuclease-I-like proteins, which are derived from, for example, prokaryotic such as Bacillus. In addition, a reformed protein which is produced by reforming one of these proteins is available so long as the reformed protein has a function similar to that of the Exonuclease-I-like protein An example of the reformed protein is one which is a gene product produced or derived from an Exonuclease-I gene by, for example, site directed mutagenesis, which includes an amino acid sequence in which one or more amino acids are made deficient, replaced, or added, and which is similar, in function, to the Exonuclease-I. In addition, a protein fragment of Exonuclease I gene (i.e. Exonuclease-I fragment) can be used provided the function is of similar to the full-length Exonuclease I.

The DNA-protein complex forming process is preferred or desired to be performed in buffer in the presence of nucleotide triphosphate or its analogs for effective formation of a stable DNA-protein complex. The buffer can be altered, for making the reaction conditions best, depending on the to-be-used recombinant protein and nuclease. For example, a tris-family buffer may be used whose pH is adjusted to about 4.0–9.0, preferably about 7.0–8.0. In general, the buffer is set to be, in concentration, about 10–100 nM, preferably about 30 nM.

As the nucleotide triphosphate or its analog, the following can be used: adenosine 5'-triphosphate (ATP), guanosine 5'-triphosphate (GTP), UTP, CTP, adenosine (γ-thio)-triphosphate (ATP-γ S), guanosine (γ-thio)- triphosphate (GTP-γ S), dATP, dUTP, and dCPT. Each of these substances is also available in combination with a nucleo diphosphate such as ADP. It is to be noted that particularly in a system for forming a DNA-protein complex if the nucleotide triphosphate such as ATP is accompanied biochemical decomposition, using the analog such as ATP-γ S of the nucleotide triphosphate is recommended or preferred. The consistency of the nucleotide triphosphate is set to be 0.1–10 nM, preferably about 5 mM.

The concentration of each of the nucleic acids (i.e. the double-stranded and single-stranded DNA) in the reaction solution can be altered so long as the former is dissolved in the latter. The ratio of the single-stranded DNA relative to the double-stranded DNA is preferred to be about 1–100 times in molar ratio.

Adding 1 molecule of the recombinant protein to 3 base sequences of the single-stranded DNA is preferable. However, it is to be noted that the optimal amount changes slightly depending on the recombinant protein per se to be added. In addition, adding about 1 unit nuclease into the double-stranded DNA per 1 μg. The optimal ratio also varies more or less depending on the nuclease per se to be added. The resulting reaction solution makes it possible to form a DNA-protein complex by being held at a temperature of 4–60° C., preferably about 37° C., for a time duration of 5 minutes or above, generally about 60 minutes.

Instead of the above-described method in which the reaction solution is added with all other substances and thereafter is held at a temperature for a time duration, the following can be employed. In detail, to begin with, the double-stranded DNA, single stranded DNA, and recombinant protein are added in the buffer which includes therein nucleotide triphosphate etc at a temperature of 4–60° C., preferably about 15 37° C., for a time duration of about 2–5 minutes or above, preferably about 10 minutes. The nuclease is added to the resulting reaction solution and is further held at a temperature of 4–60° C., preferably about 37° C., for a time duration of 5 minutes or above, generally about 30 minutes. These reaction make it possible to form a remarkable stable DNA-protein, which is likely because the Exonuclease I or the like is an enzyme which cleaves a single-stranded DNA from its end, an at-first addition of the Exonuclease I or the like into the reaction solution sometimes may delete the single-stranded DNA. However, the later addition of the Exonuclease I or the like as mentioned above makes it possible to establish an earlier or at-first bond of the recombinant protein with the single-stranded DNA, resulting in the single-stranded DNA protected or free from the Exonuclease I or the like. Thus, the single-stranded DNA is difficult to cleave, thereby making it possible to form a stable DNA-protein complex.

To deactivate the protein, one of or a combination of the following arm, added to the reaction solution: chelate agent (e.g. ethylenediaminetetraacetic acid), addition of sodium dodecyl sulfate (SDS), and starch degrading enzymes (e.g. proteinase K). Thereafter, the resulting reaction resolution is held at a temperature of about 37° C. for a time duration of 10 minutes and the triple-stranded DNA can be recovered or isolated therefrom. Such recovery or isolation can be accomplished by column chromatography or by separating the DNA temporally using methanol precipitation.

In the method for forming a triple-stranded DNA, it is preferred that the triple-stranded DNA whose substantial complementary base sequence is a 20 mer or above.

In theory, even if the complementary region of the single-stranded DNA is short, it is possible for form a 3-chain forming region by being bound to the end neighboring inclusion region. However, when the complementary region of the single-stranded DNA is too short (e.g., 20 mer or less), the formed triple-stranded DNA is not stable. On the contrary, the present invention employs a single-stranded DNA whose substantial base sequence is about a 20 mer or above. In brief forming a more stable triple-stranded DNA can be made possible. It is to be noted that employing a single-stranded DNA whose substantial base sequence is of about 30 mer or above makes it possible to make the formed triple-stranded DNA more and more stable, which is preferable.

Moreover, in each of the above-described triple-stranded DNA forming methods, the single-stranded DNA is preferred to have a base sequence which is substantially complementary to a base sequence which begins within about 20 nucleotides from the 5'-end of one of the DNA-chains of the single-stranded DNA.

As described above, so long as a single-stranded DNA includes a base sequence which is substantially complementary to a base sequence which begins at the 5'-end of one of the DNA-chains of the single-stranded DNA, binding the substantial complementary region to the end neighboring inclusion region makes it possible to forma 3-chain forming region. However, as the site to which the complementary region is bound makes a distance longer from the end of the double-stranded DNA, the 3-chain forming region is made unstable and easy to disassociate. In other words, as the region of only double-stranded increases in length, the formation of the triple-stranded DNA becomes less an less stable due to the stress caused by the double-stranded region on the triple-stranded region.

On the contrary, the present invention employs a single-stranded DNA which has a base sequence which is substantially complementary to a base sequence which begins at a within about 20 nucleotides from the 5'-end of one of the DNA-chains of the single-stranded DNA. That is, the complementary region of the single-stranded DNA is complementary to a region which begins at the very near end of the double-stranded DNA. Thus, in the formed triple-stranded DNA according to this method, the 2-chain forming region appears as an extension of the 3'-end of the single-stranded DNA in smaller length or fails to form. Thus, the structure stress resulting from the formation of the 2-chain forming region becomes difficult to generate, thereby stabilizing the 3-chain forming region. In conclusion, the present invention makes it possible to form a more and more stable triple-stranded DNA.

In particular, the single-stranded DNA is preferred to include a base sequence which is complementary to a base sequence which begins at the 5'-end of one of the DNA chains of the double-stranded DNA. This results in a 2-chain forming region not being formed on an extension of the 3'-end of the single-stranded DNA Thus, the 3-chain forming region is made stable in maximum, which makes it possible to form a most stable triple-stranded DNA. It is preferred that the complementary region of the single-stranded DNA includes a base sequence of about 60 nucleotides or less.

In the above-described method for forming a triple-stranded DNA, the recombinant protein is preferably RecA protein of *Escherichia coli* and a reformed protein which is produced by reforming this RecA protein so as to have a similar function thereto. In view of commercially availability, safety, and functionality, the RecA protein derived from *Escherichia coli* is desirable. An example of a reformed protein is one which is a gene product produced or derived from a RecA gene by, e.g., site directed mutagenesis, and includes an amino acid sequence in which one or more amino acids are made deficient, replaced, or added, and which is similar, in function, to the RecA protein. A protein fragment is also available, which is a product of reforming RecA protein gene and which is of a function similar thereto. In addition, a fragment of RecA (i.e. a RecA fragment) is also available which is of a function similar to the RecA protein.

The present invention also provides a kit for forming a triple-stranded DNA is available which includes at least either of a homologous recombinant protein and a protein having a function similar to that of the homologous recombinant protein, at least either of an Exonuclease I of *Escherichia coli* and a protein having a function similar to that of the Exonuclease I, at least either of a nucleotide triphosphate and its analogy, and a buffer.

Using the above-mentioned kit forming a triple-stranded DNA makes it possible to form a DNA-protein complex easily by way of a bond of the double-stranded DNA, the single-stranded DNA, and the Exonuclease I which is reacted in the buffer in which the nucleotide triphosphate is added. The resulting DNA-protein complex makes it possible to for a stable triple-stranded DNA by deactivating the proteins (i.e. the homologous recombinant protein, Exonuclease I, or the like).

The present invention also provides A triple-stranded DNA is made up of a linearized double-stranded DNA and a linearized single-stranded DNA including a base sequence, the base sequence being substantially complementary to a base sequence which extends from a base near 5'-end of one of DNA chains of the double-stranded DNA, the linearized double-stranded DNA and the linearized single-stranded DNA forming a 3-chain forming region in such a manner that an end neighboring inclusion region includes the 5'-end of one of DNA-chain of the double-stranded DNA being bound to a complementary region including the substantially complementary base sequence of the single-stranded DNA.

Unlike the conventional triple-stranded DNA, the newly invented triple-stranded DNA does not include protein and is formed only by the bond or coupling between the double-stranded DNA and the single-stranded DNA. The complementary region of the single-stranded DNA includes the 3-chain forming region bound to one of the end neighboring inclusion regions of the double-stranded DNA. Thus formed triple-stranded DNA can maintain its structure in stable fashion, even if more-or-less heat is applied thereto, without having to include a specially prepared substance such as protein or RecA protein. It is to be noted that the triple-stranded DNAs of the present invention also include one in which each of the end neighboring regions of the double-stranded DNA is formed with the 3-chain forming region The above-described triple-stranded DNA may be used in a southern hybridization protocol. The target DNA would be a linearized double-stranded DNA and is prepared by cleavage with a suitable restriction enzyme, while as a probe DNA the a single-stranded DNA is prepared whose 5'-end is labeled with $^{32}$p using T4 Polynucleotide Kinase and[$\gamma$-$^{32}$P] ATP. These DNA molecules are used to form a triple-stranded DNA such that the triple-stranded DNA includes a 3-chain forming region which is in the form of a bond between the complementary region of the single-stranded DNA and at least one of end neighboring inclusion regions. The triple-stranded DNA is subjected to agarose gel electrophoresis and the resulting agarose gel is placed onto a filtering paper or the like to dry with a gel drier. Then, autoradiogram of the agarose gel is taken to record a signal resulted from the probe DNA (i.e. labeled single-stranded DNA) on an X-ray film.

Thus established southern hybridization utilizing the invented triple-stranded DNA requires no additional cumbersome steps often associated with Southern hybridization techniques, such as transfer of the-agarose-gel DNA onto a membrane, immersing the resulting membrane in a probe DNA solution, and cleaning the membrane, resulting in easy doing the newly established southern hybridization for a shorter time duration, when compared to the conventional southern hybridization. This can be seen when the probe DNA is in the form of a chemically labeled single-stranded DNA which is labeled with a fluorescent material uses or the like.

The 3-chain forming region can be formed on the end neighboring inclusion region of the double-stranded DNA. However, as the 3-chain forming region moves away from the end of the double-stranded DNA, the 3-chain forming region becomes unstable and disassociates easily. When the double-stranded DNA becomes longer and is formed on the extension of the 3'-end, the structure stress which results from the existence of this double-stranded DNA makes the 3-chain forming region unstable, whereby the 3-chain forming region becomes dissociates easily. Contrary to this, according to the present invention, no 2-chain forming region is formed on the extension of the 3'-end of the single-stranded DNA which constitutes the 3-chain forming region or the 2-chain forming region is as short as 20 basepairs or less even formation thereof Thus, according to the present invention the structure stress which results from the existence of the 2-chain forming region does not form thereby resulting in stabilized 3-chain forming region. It is to be noted that the 3-chain forming region is desired to have a base sequence of about 60 nucleotides or less per unit DNA chain.

In such Southern hybridization protocols to detect the presence of nucleic acid molecules, e.&, double-stranded DNA, the method will include the following steps; an electrophoresis process for subjecting a triple-stranded DNA to agarose gel electrophoresis, the triple-stranded DNA including a linearized double-stranded DNA; and a linearized single-stranded DNA including a base sequence, the base sequence being substantially complementary to a base sequence which extends from a base near 5'-end of one of DNA chains of the double-stranded DNA, the linearize double-stranded DNA and the linearized single-stranded DNA forming a 3-chain forming region in such a manner that an end neighboring inclusion region includes the 5'-end of one of DNA-chain of the double-stranded DNA being bound to a complementary region including the substantially complementary base sequence of the single-stranded DNA; a dry process for drying the agarose gel including the triple-stranded DNA; and a detection process for detecting a signal from the agarose gel which results from the labeled single-stranded DNA.

It is to be noted that labeling the single-stranded DNA can be made with either radioactive element or chemical substance such as fluorescence material. Labeling the single-stranded DNA with radioactive element makes it possible to increase the detection ability of the southern hybridization, while labeling the single-stranded DNA with chemical substance makes it possible to perform each of the processes in safety and makes it possible to automate each of the processes.

BRIEF DESCRIPTION OF THE DRAWINGS

The above and other objects, features and advantages of the present invention will be more apparent and more readily appreciated from the following detailed description of preferred exemplary embodiments of the present invention, taken in connection with the accompanying drawings, in which;

FIG. 1 illustrates a diagram for preparing triple stranded DNA in one embodiment of the present invention FIG. 3 illustrates results of a triple-stranded-DNA-employed southern hybridization protocol (A) is an X-ray film photograph in which signals resulting from respective labeled oligonucleotide are shown and (B) is a photograph of a DNA-stained agarose gel after agarose gel electrophoresis;

FIG. 7 illustrates rusts of a triple-stranded-DNA-employed in a southern hybridization protocol (A) is an X-ray film photograph on which signals resulting from respective labeled oligonucleotide are recorded; and (B) is a photograph of a DNA-stained agarose gel after agarose gel electrophoresis.

FIG. 10 results of a triple-stranded-DNA-employed in a southern hybridization protocol (A) is an X-ray film photograph on which signals resulting from respective labeled oligonucleotide are recorded; and (B) is a photograph of a DNA-stained agarose gel after agarose gel electrophoresis.

DETAILED DESCRIPTION OF THE PRESENT INVENTION

First Embodiment

Figure 2:
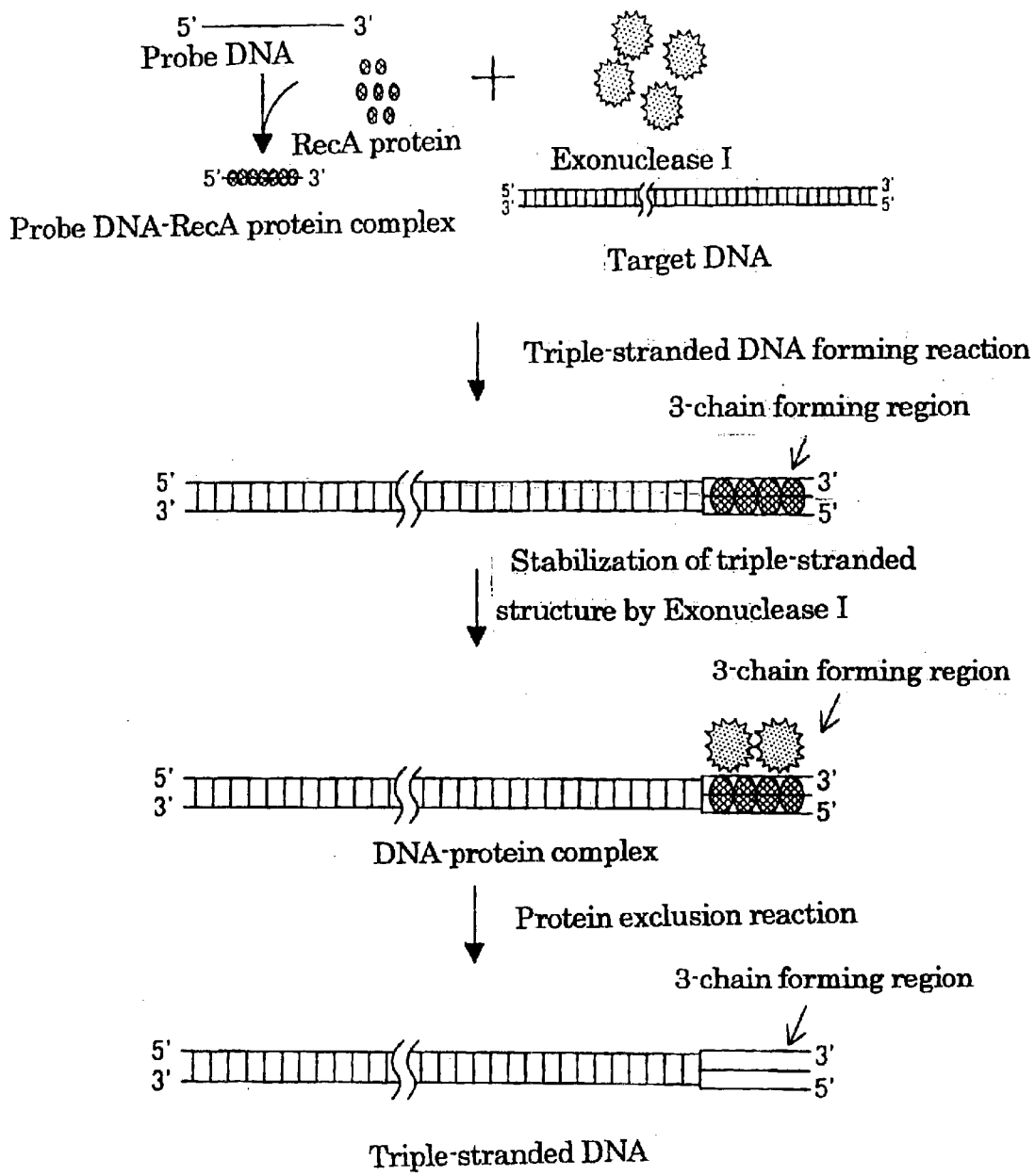
FIG. 2 illustrates the formation of a DNA-protein complex and a triple-stranded DNA

A method of forming a triple-stranded DNA and a triple-stranded DNA obtained by way of this method with reference to FIG. 1.

As target DNAs, two lands of linearized chain DNAs (i.e. a set of DNA fragment 1 and DNA fragment 2) were prepared which were obtained by cleaving pBR322 DNA (4.4 kbp), as a kind of circular plasmid, with restriction enzymes Sca I and Nru I, respectively. The DNA fragment 1 and the DNA fragment 2 are of about 2.9 kbp and about 1.5 kbp, respectively.

As illustrated in FIG. 1, as a probe DNA, a complementary single-stranded DNA ( oligonucleotide 1 (SEQ ID NO: 1)) was prepared in the vicinity of a cleavage site from Sca I of the DNA fragment 1. In detail, the prepared oligonucleotide 1 includes a base sequence of 60 mer which is 100% complementary to a base sequence which begins at a 5'-end of the DNA chain which locates near a side of the cleavage site of Sca I.

In addition, as another probe DNA, a complementary single-stranded DNA ( oligonucleotide 2 (SEQ ID NO: 2)) was prepared in the vicinity of a cleavage site from Sca I of the DNA fragment 1. In detail, the prepared oligonucleotide 2 includes a base sequence of 60 mer which is 100% complementary to a base sequence which begins at a 5'-end of the DNA chain which locates near a side of the cleavage site of Sca I.

By way of well-known methods, the oligonucleotides 1 and 2 can be synthesized or produced on the basis of the base sequences of the DNA fragments 1 and 2, respectively.

Thereafter, the oligonucleotides 1 and 2 were labeled at 5'-ends thereof with $^{32}$p with usage of T4 Polynucleotide kinase and [$\gamma$-$^{32}$]ATP.

oligonucleotide 1 (SEQ ID NO: 1):
   5'-cact gcataatct cttactgcta tgccatccgt aagatgcttt tctgtgactg gtgagt-3' oligonucleotide 2 (SEQ ID NO: 2):
   5'-acgccgggca agagcaactc ggtcgccgca tacactattc tcagaatgac ttggttgat-3'

As a recombinant protein and a nuclease, a RecA protein of *Escherichia coli* and an Exonuclease I of *Escher coli* were pod As a nucleoside triphosphoric acid or its analog. ATP-$\gamma$ S was prepared As a buffer solution, a solution was prepared which contains magnesium acetate and tri-acetate.

In a DNA-protein complex forming process, as shown in FIG. 2, 200 ng of the target DNAs (i.e. the DNA fragments 1 and 2), the labeled probe DNAs (i.e. 1 pmol of the labeled oligonucleotide 1 and 1 pmol of the labeled oligonucleotide 2), 3.0 μg of the RecA protein, and 4 units of Exonuclease I are placed in a mixture of 4.8 mM of the ATP- $\gamma$ S, 20 mM of the magnesium acetate and 30 mM of the tris-acetate (pH:7.2) and were held at a temperature of 37° C. for a time duration of 30 minutes. The total amount of the reacted solutions was about 20 μlitters.

It is to be noted that FIG. 2 is a simplified drawing in which only one of two combinations of the target DNA and the probe DNA.

Thus, two kinds of DNA-protein complexes were formed or produced. In detail, near the vicinity region of the end of the cleavage site from Sca I of the DNA fragment 1, the DNA-protein complex was formed to which the whole of the oligonucleotide I was bounded such that at least the RecA protein was involved in, while near the vicinity region of the end of the cleavage site from Sca I of the DNA fragment 2 the other DNA-protein complex was formed to which the whole of the oligonucleotide 2 was bounded such that at least the RecA protein was involved in.

More specifically, first of all, the RecA protein was bound to the oligonucleotide 1 (the probe DNA 1) to form the probe DNA-RecA protein complex. Then, the resultant probe DNA-RecA protein complex was bound to the DNA fragment 1 (the target DNA 1) to form the DNA-protein complex. During such a formation of the DNA-protein complex, oligonucleotide 1 was believed to bind to the region including base sequence which is complementary to the oligonucleotide I (i.e. the vicinity region of the end of the cleavage site from Sca I) at least in participation of the RecA protein. The Exonuclease I was believed to stabilize the DNA-protein complex.

Likewise, the RecA protein was bound to the oligonucleotide 2 (the probe DNA 2) to form the other probe DNA-RecA protein complex. Then, the resultant probe DNA-RecA protein complex was bound to the DNA fragment 2 (the target DNA 2) to form the other DNA-protein complex. During such a formation of the other DNA-protein complex, oligonucleotide 2 was believed to bind to the region including base sequence which is complementary to the oligonucleotide 2 (i.e. the vicinity region of the end of the cleavage site from Sca I) at least in participation of the RecA protein. The Exonuclease I was believed to stabilize the other DNA-protein complex.

Each of these DNA-protein complexes mains relatively stable despite of having 3-chain forming region.

Next, in a protein deactivating process, this reaction solution was added with 0.5%(W/Vol) of the SDS and 0.7 mg/ milliliter of the proteinase K and the resultant mixture was held at 37° C. for a time duration of 30 minutes to deactivate both the RecA protein and the Exonuclease I.

Thus, two kinds of triple-stranded DNAs were formed That is to say, the triple-stranded DNA having 3-chain forming region was formed to which the whole of the oligonucleotide I was bounded at the vicinity region of the end of the cleavage site from Sca I of the DNA fragment 1, while the other triple-stranded DNA having 3-chain forming region was formed to which the whole of the oligonucleotide 2 was bounded at the vicinity region of the end of the cleavage site from Sea I of the DNA fragment 2.

As previously mentioned, conventionally, even if a DNA-protein with 3-chain forming region was formed, deactivating the protein brought in deletion of the 3-chain forming region, thereby separating into the target DNA (double-stranded DNA) and the probe DNA (single-stranded DNA).

To the contrary, in the first embodiment 1, even if the protein (each of the RecA protein and the Exonuclease I) was deactivated, the triple-stranded DNA remained stable. Such the triple-stranded is free from a special substance such as protein to maintain its structure stably and remains its stable structure even despite of more or less heat application thereto.

It is to be noted that preparing a kit is very convenient which includes a homologous recombinant protein such as a RecA protein, an Exonuclease I, a nucleoside triphosphoric acid such as ATW-$\gamma$ S, a buffer containing tris-acetate, and others. The reason is that using such a kit makes it possible to form a triple-stranded DNA easily even if each of the target DNA and the prove DNA is changed in kind.

Next, an explanation will be made with respect to Southern hybridization using the above-mentioned triple-stranded DNA.

First of all, according to the above-explained method, two kinds of triple stranded DNAs were formed.

Then, an electrophoresis process was performed in which a half amount (about 10 μlitters) of the reaction solution was subjected to 1% agarose gel electrophoresis. The resulting agarose gel electrophoresis was immersed in a solution of ethidium bromide to stain the DNA in the agarose gel therewith. Thereafter, the resultant DNA was taken with a picture to record. The result appears on lane 2 in FIG. 3(B).

Next, in a dry process, the resultant agarose gel was placed on a filter paper and was put into a gel drier to dry.

Thereafter, in a detection process, an autoradiogram of the dried agarose gel was taken to record signals on an X-ray film which were resulted from the labeled oligonucleotides 1 and 2. The results appear on lane 2 in FIG. 3(A).

In FIGS. 3(A) and 3(B), the detected signal which appears at an upper portion near about 2.9 kbp results from the triple stranded DNA in which the oligonucleotide 1 is bound to the DNA fragment 1, while the other detected signal which appears at a lower portion near about 1.5kbp results from the other triple-stranded DNA in which the oligonucleotide 2 is bound to the DNA fragment 2.

Such a Southern hybridization, when compared to the conventional Southern hybridization, makes it possible to eliminate skilled and/or operations such as a transfer of the DNA in the agarose gel to a membrane, an immersion of this membrane in a probe DNA solution, and washing the membrane. Thus, conducting or doing Southern hybridization can be established easily and in a shorter time duration.

A comparative experiment whose results are indicated in FIG. 3 will be hereinbelow described.

Lane M indicates a DNA size marker having scale markings as indicated at a left side in the drawing.

This lane M is obtained in such a manner that a DNA was cleaved with a restriction enzyme HindIII and thereafter each 5'-end of the DNA fragment were labeled with 32P using T4 Polynucleotide kinase and[γ-32]ATP.

Lane 1 indicates a result of a reaction which is similar to the above reaction followed by lane 2 result except that in the former the above DNA-protein complex forming process employed an addition of 4-unit Mug Bean nuclease instead of adding Exonuclease I. Other processes of the reaction followed by lane 1 result were identical to those of the reaction followed by the lane 2 result.

Lane 3 indicates a result of a reaction which is similar to the above reaction followed by lane 2 result except that in the former the above DNA-protein complex forming process employed an addition of 4-unit Exonuclease III instead of adding Exonucleance I. Other processes of the reaction followed by lane 3 result were identical to those of the reaction followed by the lane 2 result Lane 4 indicates a result of a reaction which is similar to the above reaction followed by lane 2 result except that in the former the above DNA-protein complex forming process employed an addition of 4-unit T4 PNK instead of adding Exonucleance I. Other processes of the reaction followed by lane 4 result were identical to those of the reaction followed by the lane 2 result.

Lane 5 indicates a result of a reaction which is similar to the above reaction followed by lane 2 result except that in the former the above DNA-protein complex forming process employed an addition of 4-unit T4 DNA Ligase instead of adding Exonucleance I. Other processes of the reaction followed by lane 5 result were identical to those of the reaction followed by the lane 2 result Lane 6 indicates a result of a reaction which is similar to the above reaction followed by lane 2 result except that in the former the above DNA-protein complex forming process did not employ an addition of Exonucleance I. Other processes of the reaction followed by lane 6 result were identical to those of the reaction followed by the lane 2 result As can be apparently understood from FIG. 3(A) indicating results, the signal is detected at only lane 2, while no signals are detected at other lanes 1, 3 to 6 inclusive. The results of lanes 2 and 6 results prove that forming a stable triple-stranded DNA requires Exonucleance I in the DNA-protein complex forming process. In addition, the results of lanes 1, 3, 4, and 5 indicate that it is impossible to form a stable triple-stranded DNA even by using Mug Bean nuclease, Exonucleance III, T4 PNK, and T4 DNA Ligase as alternatives of Exonucleance I. Thus, it is believed to form a stable triple-stranded DNA the DNA-protein complex forming press requires Exonucleance I or a protein having a similar function thereto.

Second Embodiment

Hereinafter a second embodiment of the present invention will be described such that explaining its portions similar to those of the first embodiment is made simplified or omitted.

Figure 4:
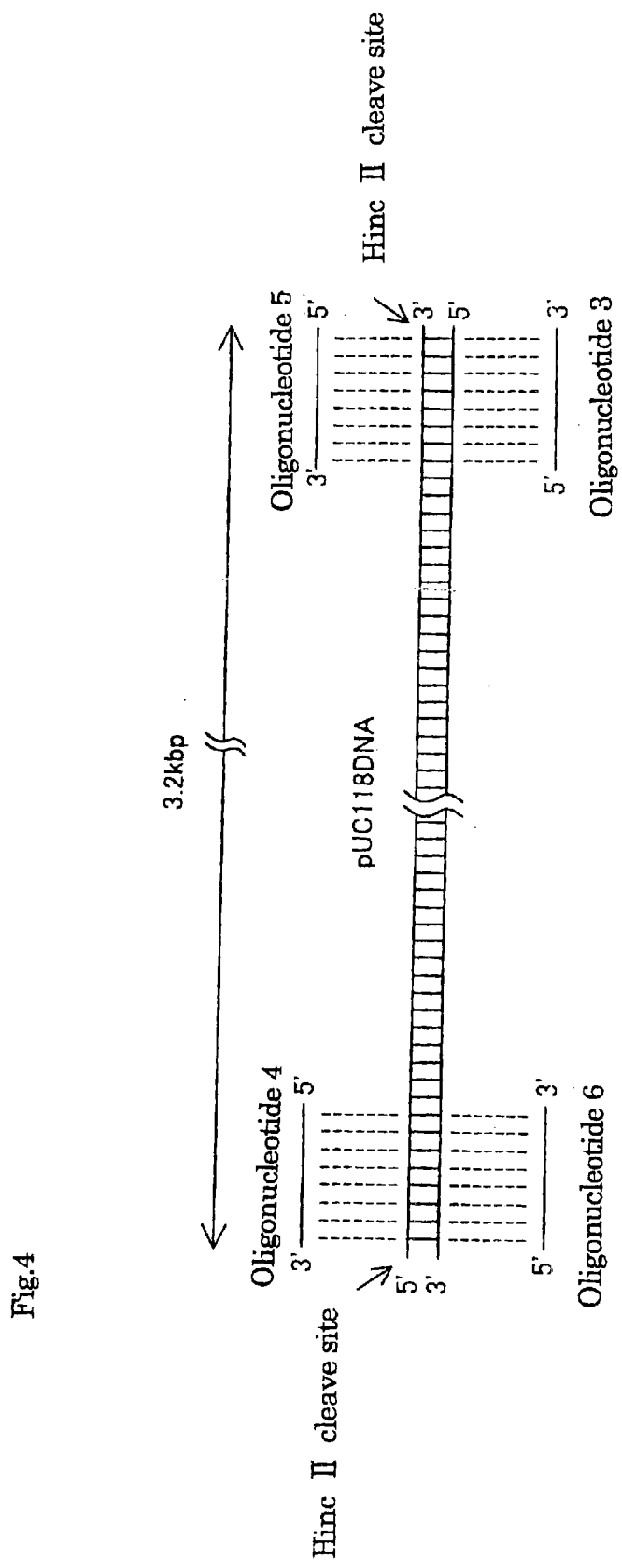
FIG. 4 illustrates the formation of another embodied triple-stranded DNA

As shown in FIG. 4, as target DNAs, linearized double-stranded DNAs were prepared which were obtained by cleaving a pUC118 DNA (about 3.2 kkbp), a kind of circular plasmid DNA, with a restriction enzyme HincII. It is to be noted that GeneBank Access Number, U07650 should be refereed as to the base sequence of pUC118 DNA.

In addition, as shown in FIG. 4, as a probe DNA, a single-stranded DNA ( oligonucleotide 3 [SEQ ID NO:3]) was prepared which was complementary to end neighboring region (a right side in the drawing) of one of the target DNAs. In detail, the oligononucleotide 3 was prepared which includes a base sequence of 60 mer which is 100% complementary to a base sequence of 60 mer which begins at a 5'-end of the DNA chain (at a lower side in the drawing). The oligononucleotide 3 was labeled at 5'-end thereof with 32P with usage of T4 Polynucleotide kinase and [γ-32P] ATP.

oligononucleotide 3:

5'-cgacgttgta aaacgacggc cagtgaattc gagctcggta cccggg-
gatc ctctagagtc-3' (SEQ ID NO:3)

Next, in a DNA-protein complex forming process, as shown in FIG. 2, 200 ng of the target DNA (i.e. the single-stranded pUC118 DNA), 1 pmol of the labeled probe DNA (i.e. the labeled oligonucleotide 3), 3.0 μg of the RecA protein, and 4 units of Exonuclease I are placed in a mixture of 4.8 mM of the AT-γ S, 20 mM of the magnesium acetate and 30 mM of the tris-acetate (pH:7.2) and were held at a temperature of 37° C. for a time duration of 30 minutes. Thus, similar to the above-described First Embodiment, a DNA-protein complex was formed. That is to say, near the vicinity region of the end (right side in the drawing) of the cleavage site from the target DNA, the DNA-protein complex was formed which is stable and to which the whole of the oligonucleotide 3 was bound such that at least the RecA protein was involved in (cf.FIG. 2). This triple-stranded is also capable of remaining its structure without any specially prepared protein and is capable of remaining its structure in stable fashion even if more or less a heat is applied to.

Then an electrophoresis process was performed in which a half amount (about 10μlitters) of the reaction solution was subjected to 1% agarose gel electrophoresis. The resulting agarose gel electrophoresis was immersed in a solution of ethidium bromide to stain the DNA in the agarose gel therewith. Thereafter, the resultant DNA was taken a picture to record. The result appears on lane 1 in FIG. 5(B).

Next, like the First Embodiment, in a dry process, the resultant agarose gel was placed on a filter paper and was put into a gel drier to dry.

Thereafter, in a detection process, an autoradiogram of the dried agarose gel was taken to record signals on an X-ray film which were resulted from the labeled oligonucleotide 3. The results appear on lane 1 in FIG. 5(A).

Figure 5A:
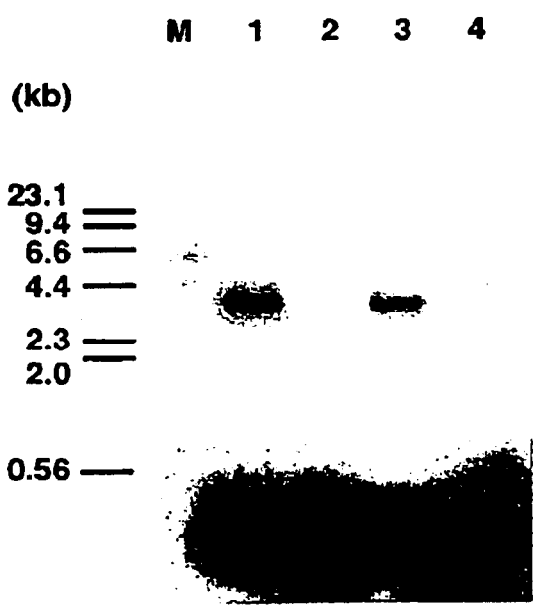
FIG. 5 illustrates rusts of a triple-stranded-DNA employed in a southern hybridization (A) is an X-ray film photograph on which signals resulting from respective labeled oligonucleotide are recorded; and (B) is a photograph of a DNA-stained agarose gel after agarose gel electrophoresis.
Figure 5B:

In FIGS. 5(A) and 5(B), the detected signals which appear at an upper portion near about 3.2 kbp result from the triple-stranded DNA in which the oligonucleotide is bound to the target DNA Such a Southern hybridization, which is similar to that in the above-explained First Embodiment, when compared to the conventional Southern, makes it possible to eliminate skilled and/or operations such as a transfer of the DNA in the agarose gel to a membrane, an immersion of this membrane in an probe DNA solution, and washing the membrane. Thus, conducting or doing Southern hybridization can be established easily and in a shorter time duration On the other hand, as shown in FIG. 4, as another probe DNA, a single-stranded DNA ( oligonucleotide 4 [SEQ ID NO:4]) was prepared which was complementary to the other end neighboring region (a left side in the drawing) of the target DNA In detail, the oligononucleotide 4 was prepared which includes a base sequence of 60 mer which is 100% complementary to a base sequence of 60 mer which begins at a 5'-end of the DNA chain (at an upper side in the drawing). The oligononucleotide 4 was labeled at 5'-end thereof with 32P with usage of T4 Polynucleotide kinase and [γ-32P] ATP.

oligononucleotide 4:

5'-caatttcaca caggaaacag ctatgaccat gattacgcca agcttgcatg cctgcaggtc-3' (SEQ ID NO:4) And, a DNA-protein complex forming process is performed similar to the First Embodiment except for using the labeled oligononucleotide 4 instead of the labeled oligononucleotide 3 to form, near the vicinity region of the other end (left side in the drawing) of the cleavage site from the target DNA, the DNA-protein complex which is stable and to which the whole of the oligonucleotide 4 was bound such that at least the RecA protein was involved in( cf.FIG. 2).

Thereafter, performing the protein deactivating process was performed to form a triple-stranded DNA (cf.FIG. 2) which had the 3-chaing forming region near the vicinity region of the other end (left side in the drawing) of the cleavage site from the target DNA, the 3-chaing forming region being bound with the whole of the oligonucleotide 4. Needless to say, this triple-stranded DNA is also stable.

Then, an electrophoresis process was performed and the stained DNA was taken with a picture, to record The result appears on lane 3 in FIG. 5(B). Thereafter, like the above-explained First Embodiment, dry and detection processes were performed. The results appear on lane 3 in FIG. 5(B).

Next, a comparative experiment whose results are indicated in FIG. 5 will be hereinbelow described.

Lane M is, like the above-described First Embodiment, a DNA size marker.

Lane 2 indicates results of a reaction which is similar to the above-described reaction followed by lane 2 results except that in the former the above DNA-protein complex forming process employed an addition of a labeled oligonucleotide 5 [SEQ ID NO: 5] as a labeled probe DNA This oligonucleotide 5 is, as apparent from FIG, 4, in the form of a single-stranded DNA which was complementary to the end neighboring region (the right side in the drawing) of the target DNA However, unlike the oligonucleotide 3, the oligonucleotide 5 includes a base sequence of 60 mer which is 100% complementary to a base sequence of 60 mer which begins at a 3' end of the DNA chain (at an upper-right side in the drawing). It is to be noted that the labeling method of the oligonucleotide 5 was identical with that of each of the oligonucleotides 3 and 4.

oligonucleotide 5:

5'-gactctagag gatccccggg taccgagctc gaattcactg gccgtcgttt tacaacgtcg-3' (SEQ ID NO:5)

Lane 4 indicates results of a reaction which is similar to the above-described reaction followed by lane 1 results except that in the former the above DNA-protein complex forming process employed an addition of a labeled oligonucleotide 6[SEQ ID NO:6] as a labeled probe DNA. This oligonucleotide 6 is, as apparent from FIG. 4, in the form of a single-stranded DNA which was complementary to the other end neighboring region (the left side in the drawing) of the target DNA. However, unlike the oligonucleotide 4, the oligonucleotide 6 includes a base sequence of 60 mer which is 100% complementary to a base sequence of 60 mer which begins at a 3' end of the DNA chain (at a lower-left side in the drawing). It is to be noted that the labeling method of the oligonucleotide 6 was identical with that of each of the oligonucleotides 3, 4 and 5.

oligonucleotide 6:

5'-gacctgcagg catgcaagct tggcgtaatc atggtcatag ctgtttcctg tgtgaattg-3' (SEQ ID NO:6)

As apparent from FIG. 5(A), signals can be found or detected on lanes 1 and 3, while no signals can be found or detected on lanes 2 and 4. The results from lanes 1 and 3 prove that forming the 3-chain forming region can be established at either end neighboring region. However, the results of lanes 2 and 4 indicates that forming a stable triple-stranded is impossible when the probe DNA is complementary to the base sequence at the end neighboring region of the 3' end of the DNA chain of one of the target DNAs. Thus, it is believed that for forming a stable triple-stranded DNA should be complementary to the base sequence at the end neighboring region of the 5'-end of the DNA chain of one of the target DNAs. Indeed, it is known that as understood lanes 2 and 4 forming a stable DNA-protein complex is possible in the DNA-protein complex forming process even if the probe DNA is complementary to the base sequence at the end neighboring region of the 3' end of the DNA chain of one of the target DNAs. However, even in such a case, no stable triple-stranded DNA can be formed due to the fact that the 3-chain forming region is made disappeared or deleted when RecA protein and Exonuclease are deactivated in the protein deactivating process Third Embodiment Hereinafter a third embodiment of the present invention will be described such that explaining its portions similar to those of the first embodiment is made simplified or omitted.

A comparative experiment whose results are indicated in FIG. 6 will be hereinbelow described Lane M is, like the above-described Embodiments, a DNA size marker.

Lane 1 indicates results of a reaction which is similar to the above-described reaction of the second embodiment followed by lane 2 results (cf.FIG. 5). In detail, as target DNAs, linearized double-stranded DNAs were prepared which were obtained by cleaving a pUC118 DNA (about 32 kkbp) with a restriction enzyme Hinc II. A probe DNA is selected such that it is complementary to the base sequence at the end neighboring region of the 3' end of the DNA chain of one of the target DNAs the labeled oligonucleotide 5 (cf.FIG. 4). And, in the DNA-protein complex forming process, the reaction solution was held at a temperature for 30 minutes.

Lane 2 indicates results of a reaction which is similar to the reaction followed by the lane 1 results but in the former reaction the reaction solution was held at a tempt for 60 minutes in the DNA-protein complex forming process. Lane 3 indicates results of a reaction which is similar to the reaction followed by the lane 1 results but in the former reaction the reaction solution was held at a temperature for 120 minutes in the DNA-protein complex forming process.

Lane 4 indicates results of a reaction which is similar to the reaction followed by the lane 1 results but in the former reaction the reaction solution was held at a temperature for 180 minutes in the DNA-protein complex forming process.

Lane 5 indicates results of a reaction which is similar to the above-described reaction of the second embodiment followed by lane 2 results (cf.FIG. 5). In detail, as target DNAs, linearized double-stranded DNAs were prepared which were obtained by cleaving a pUC118 DNA with a restriction enzyme Hinc II. A probe DNA is selected such that it is complementary to the base sequence at the end neighboring region of the 3' end of the DNA chain of one of the target DNAs i.e. the labeled oligonucleotide 3 (cf.FIG. 4). And, in the DNA-protein complex forming process, the reaction solution was held at a temperature for 30 minutes.

Lane 6 indicates results of a reaction which is similar to the reaction followed by lane 5 results but in the former reaction the reaction solution was held at a temperature for 60 minutes in the DNA-protein complex forming process.

Lane 7 indicates results of a reaction which is similar to the reaction followed by lane 5 results but in the former reaction the reaction solution was held at a temperature for 120 minutes in the DNA-protein complex forming process.

Lane 8 indicates results of a reaction which is similar to the reaction followed by lane 5 results but in the former reaction the reaction solution was held at a temperature for 180 minutes in the DNA-protein complex forming process.

Figures 6A, 6B:
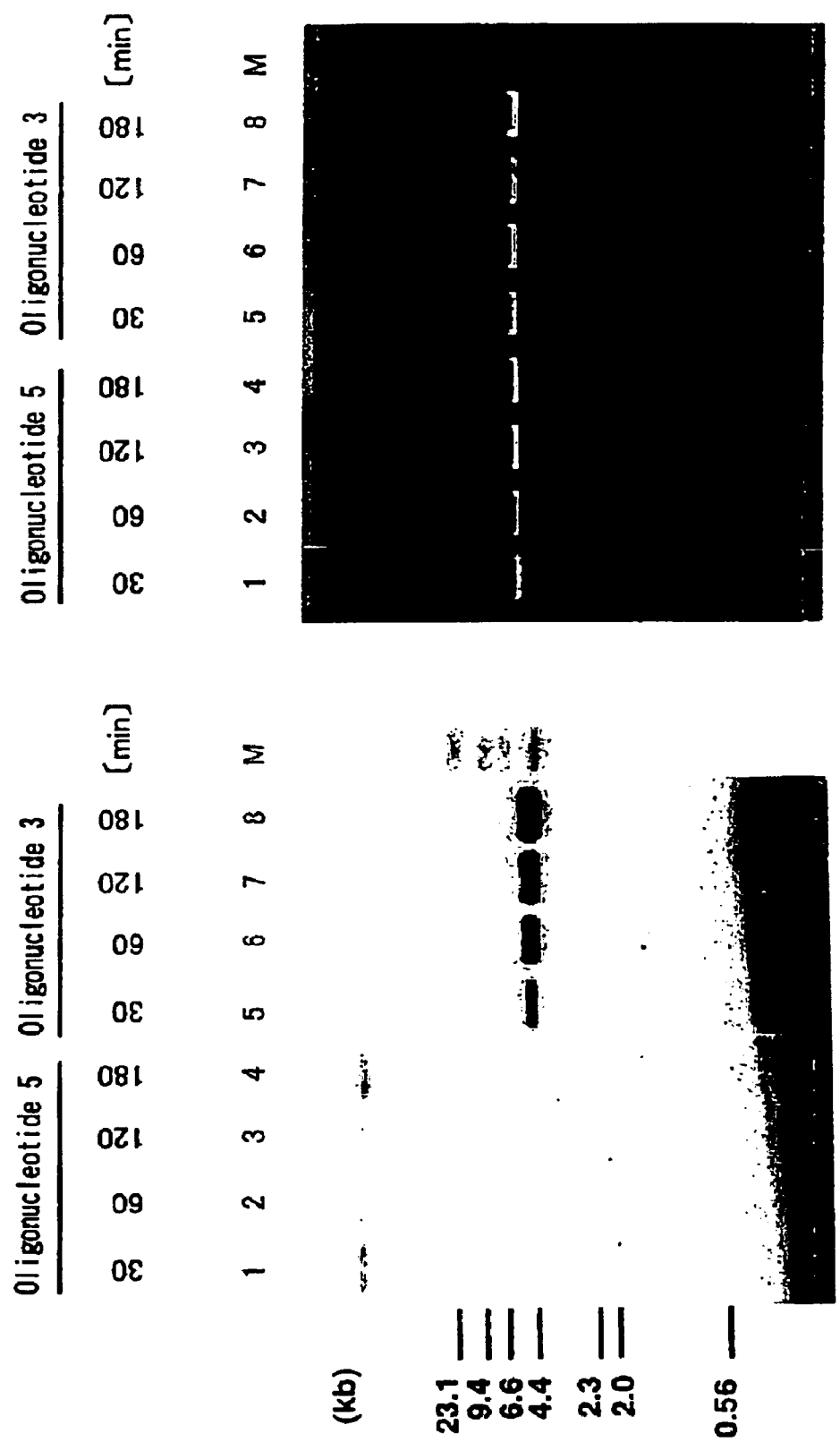
FIG. 6 illustrates results of a triple-stranded-DNA-employed in a southern hybridization protocol (A) is an X-ray film photograph on which signals resulting from respective labeled oligonucleotide are recorded and (B) is a photograph of a DNA-stained agarose gel after agarose gel electrophoresis.

As FIG. 6(A) indicates, no signals are found or detected on lanes 1, 2, 3, and 4, while signals are found or detected on lanes 5,6,7, and 8. The signals on lanes 5,6,7, and 8 change such that the signal intensity increases as the lane number ascends i.e. the signals at lanes 5 and 8 are minimum and maximum, respectively.

According to lane 1–4 results, when the probe DNA is complementary to the base sequence at the end neighboring region of the 3' end of the DNA chain of one of the target DNAs, it can be found that even if the reaction time duration for the DNA-protein forming process is made longer, forming a stable triple-stranded DNA is unsuccessful or impossible.

On the other hand, according to lane 5–8 results, when the probe DNA is complementary to the base sequence at the end neighboring region of the 5' end of the DNA chain of one of the target DNAs, it can be found that even if the reaction time duration for the DNA-protein forming process is comparatively short (e.g. 30 minutes), forming a stable triple-stranded DNA is possible or successful. Though an indication of experimental results is omitted, it is observed that forming a stable triple-stranded DNA is possible or successful even though the reaction time duration is set to be about 5 minutes. In addition, in the DNA-protein forming process, making its reaction time duration is made longer brings in much quantity of a formed stable triple-stranded DNA. A remarkable signal intensity difference is found between 30 and 60 minutes, while little signal intensity difference is found between 60 and 120 minutes (between 120 and 180 minutes). Thus, it can be believed that for about 60 minutes most of the target DNAs (i.e. the double-stranded DNAs) changes into the triple-stranded DNAs. Therefore, the reaction time duration in the DNA-protein is preferred to be not less than 5 minutes and in particular the reaction time duration of about 60 minutes seems to be adequate.

Fourth Embodiment

Hereinafter a fourth embodiment of the present invention will be described such that explaining its portions similar to those of the above-described embodiments is made simplified or omitted.

A comparative experiment whose results are indicated in FIG. 7 will be hereinbelow described.

Lane M is, like the above-described Embodiments, a DNA size marker.

Lane 1 indicates results of a reaction which is similar to the above-described reaction of the third embodiment followed by lane 1 results (cf.FIG. 6) except that in the former no ATP-γ S was added. In detail, as target DNAs, linearized double-stranded DNAs were prepared which were obtained by cleaving a pUC118 DNA with a restriction enzyme Hinc II. A probe DNA is selected such that it is complementary to the base sequence at the end neighboring region of the 3' end of the DNA chain of one of the target DNAs i.e. the labeled oligonucleotide 5 (cf.FIG. 4). And, in the DNA-protein complex forming process, the reaction solution was held at a temperature for 30 minutes.

Lane 2 indicates results of a reaction which is similar to the reaction of the third embodiment followed by lane 2 (cf.FIG. 6) results but in the former reaction no ATP-γ S was added and the reaction solution was held at a temperature for 60 minutes in the DNA-protein complex forming process.

Lane 3 indicates results of a reaction which is similar to the reaction of the third embodiment followed by lane 2 (cf.FIG. 6) results but in the former reaction no ATP-γ S was added and the reaction solution was held at a temperature for 120 minutes in the DNA-protein complex forming process.

Lane 4 indicates results of a reaction which is similar to the reaction of the third embodiment followed by lane 3 results but in the former no ATP-γ S was added and reaction the reaction solution was held at a temperature for 180 minutes in the DNA-protein complex forming process.

Lane 5 indicates results of a reaction which is similar to the above-described reaction of the third embodiment followed by lane 5 results (cf.FIG. 6) except that in the former no ATP-γ S was added A probe DNA is selected such that it is complementary to the base sequence at the end neighboring region of the 5'-end of the DNA chain of one of the target DNAs i.e. the labeled oligonucleotide 3. In the DNA-protein complex forming process, the reaction solution was held at a temperature for 30 minutes.

Lane 6 indicates results of a reaction which is similar to the reaction of the third embodiment followed by lane 6 results (cf.FIG. 6) but in the former reaction no ATP-γ S was added and the reaction solution was held at a temperature for 60 minutes in the DNA-protein complex forming process.

Lane 7 indicates results of a reaction which is similar to the reaction of the third embodiment followed by lane 7 results (cf.FIG. 6) but in the former reaction no ATP-γ S was added and the reaction solution was held at a temperature for 120 minutes in the DNA-protein complex forming process.

Lane 8 indicates results of a reaction which is similar to the reaction of the third embodiment followed by lane 8 results (cf.FIG. 6) but in the former reaction no ATP-γ S was added and the reaction solution was held at a Janice for 180 minutes in the DNA-protein complex forming process.

As FIG. 7(A) indicates, no signals are found or detected on lanes 1–8. In the present embodiment whose DNA-protein complex forming process was performed without an addition of ATP-γ S, it is easily forecasted that lane 1–4 of the results fails to indicate signals (i.e. to form a triple-stranded DNA) in light of no signal detection (no formation of a triple-stranded DNA) from lane results 1–4 of the third embodiment whose DNA-protein complex forming process was performed with an addition of ATP-γ S.

On the other hand, signals can be detested from lane results 5 - 8 of the third embodiment whose DNA-protein complex forming process was performed with an addition of ATP-γ S, whereas no signals can be detected from lane results 5–8 of the present embodiment despite of making the reaction time longer. Thus, it is proved that in the DNA-protein forming process adding an addition of ATP-γ S is required or essential.

In summary, in a case where at least RecA protein and Exonuclease I are employed as recombinant protein and nuclease, respectively, the DNA-protein complex forming process seems to have to require ATP-γ S or substance having a function similar thereto seems to be required. However, according to another experiment (cf. a sixth embodiment which will be detailed later) result, a small amount of triple-stranded DNA is formed without ATP-γ S. That is to say, the formation rate is about 1/50–1/100 when compared to formation of triple-stranded DNA with ATP-γ S. Thus, for forming a triple stranded-DNA, it is not able to conclude that ATP-γ S or substance having a function similar thereto is essential. However, performing the DNA-protein complex forming process is desired to perform with an addition of ATP-γ S for effective formation of a stable triple stranded-DNA.

Fifth Embodiment

Hereinafter a fifth embodiment of the present invention will be described such that explaining its portions similar to those of the above-described embodiments is made simplified or omitted.

Figure 8A:
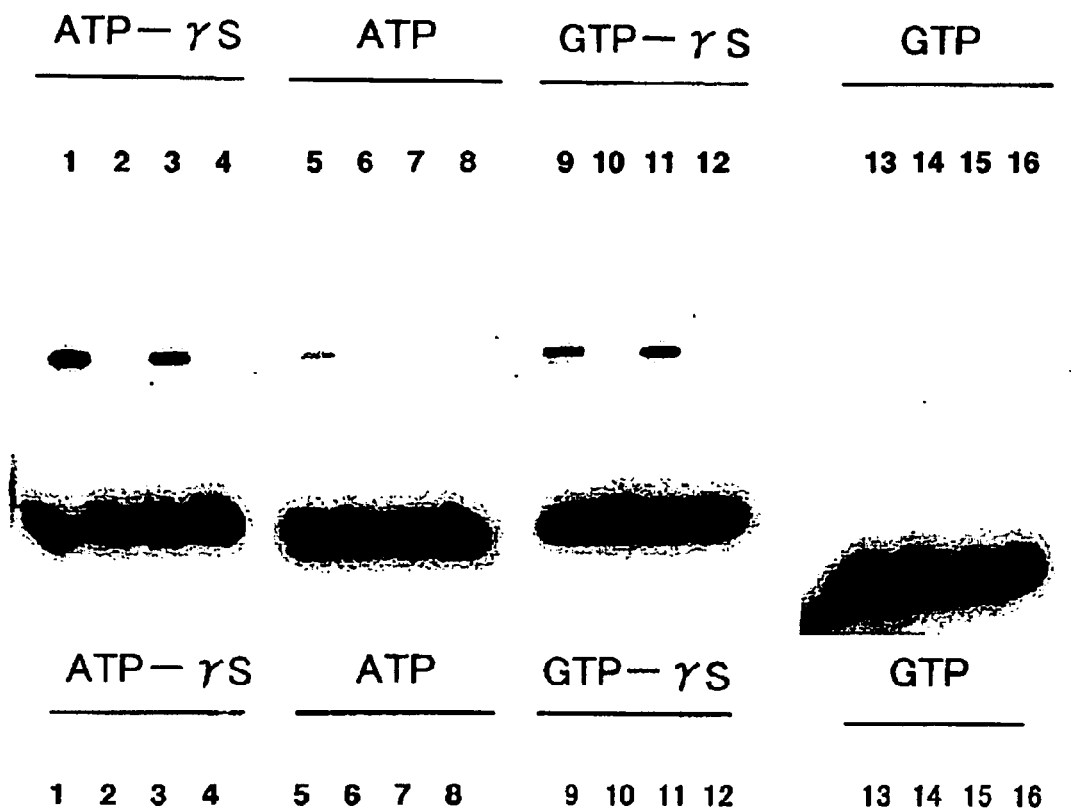
FIG. 8 illustrates results of a triple-stranded-DNA-employed in a southern hybridization protocol (A) is an X-ray film photograph on which signals resulting from respective labeled oligonucleotide are recorded; and (B) is a photograph of a DNA-stained agarose gel after agarose gel electrophoresis.
Figure 8B:
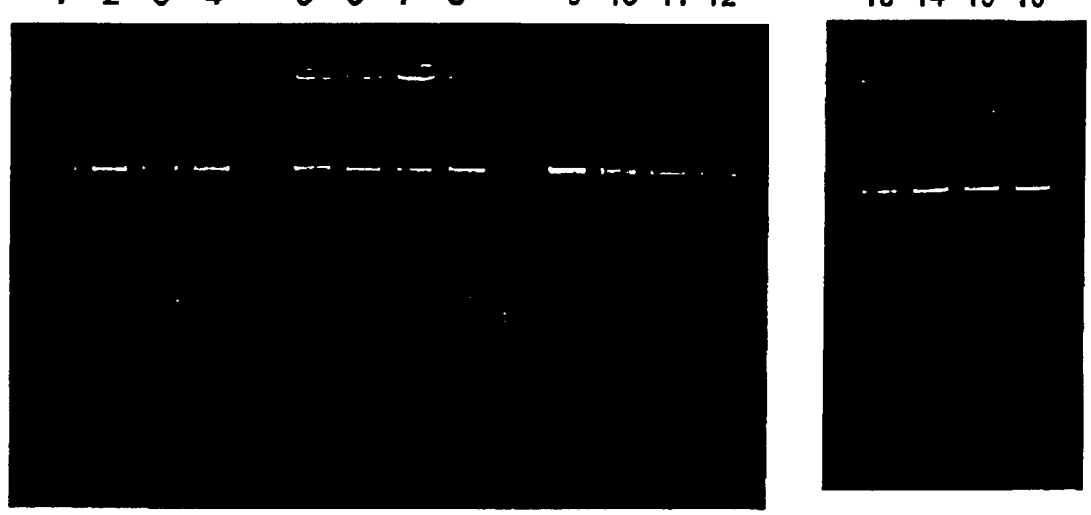

A comparative experiment whose results are indicated in FIG. 8 will be hereinbelow described Lanes 1–4 indicate results of each of reactions which are similar to the above-described reactions of the second embodiment followed by lane 1–4 results (cf.FIG. 5). In detail, in the DNA-protein complex forming process, a target DNA (i.e. a linearized pUC118 DNA), a labeled oligonucleotide 3,4,5, or 6, and a RecA protein an Exonuclease I are brought into reaction with in a mixture of ATP-γ S, magnesium acetate, and tris-acetate. Lanes 1, 2, 3, and 4 indicates results when the labeled oligonucleotide 3, the labeled oligonucleotide 5, the labeled oligonucleotide 4, and the labeled oligonucleotide 6 were used, respectively (cf.FIG. 4).

Lanes 5–8 indicate results of reactions which were similar to the above-mentioned reactions followed by lane 1–4 results except that instead of ATP-γ S 4.8 mM of ATP was added as nucleoside-triphosphate or it analog in the DNA-protein complex forming process.

Lanes 9–12 indicate results of reactions which were similar to the above-mentioned reactions followed by lane 1–4 results except that instead of ATP-γ S 4.8 mM of GTP-γ S was added as nucleoside-triphosphate or it analog in the DNA-protein complex forming process.

Lanes 13–16 indicate results of reactions which were similar to the above-mentioned reactions followed by lane 1–4 results except that instead ATP-γ S 4.8 mM of GTP-γ S was added as nucleoside-triphosphate or its analog in the DNA-protein complex forming process.

As FIG. 8(A) indicates, apparently, signals are detected on lanes 1, 3, 5, 7,9, and 11, while on others i.e. lanes 2, 4, 6, 8, 10, 12, and 13–16 no signals are detected. Lane 1–4 results of the present embodiments are identical to lane 1–4 results of the second embodiment due to the fact that the former came from the reactions which were similar to those followed by the latter (cf.FIG. 5).

On lanes 5–8, signals are detected, though these signals are weak in intensity, similar to lanes 1–4. Thus, it is proved that forming a stable triple-stranded DNA can be attained even if ATP is used as nucleoside-triphosphate or it's analog in the DNA-protein complex process.

On lanes 9–12, signals are detected, which are similar, in intensity, to signals detected on lanes 1–4. Thus, it is proved Fat forming a stable triple-stranded DNA can be attained even if GTP-γ S is used as nucleoside-triphosphate or it's analog in the DNA-protein complex process.

No signals are detected on found on lanes 13–16. Thus, it is proved that even if GTP is used as nucleoside-triphosphate or its analog in the DNA-protein complex process forming an amount of triple-stranded DNA is impossible which is above detection level.

As apparent from the above-description, it can be thought that for forming a stable triple-stranded DNA an adequate selection of nucleoside-triphosphate or its analog is preferred. That is to say, in case of using RecA protein and Exonuclease I, it can be thought that using ATP-γ S, ATP, or GTP-γ S is preferable, and particularly using ATP-γ S or GTP-γ S is very preferable.

However, the reason why the formed amount of triple-stranded DNA became smaller when used ATP seems to a biochemical decomposition of ATP in the reaction solution. This results in that selecting a reaction solution which is free from such biochemical decomposition is thought to make it possible to increase a formed amount of triple-stranded DNA even if ATP is used In addition, similar experiments were conducted in which UTP and CTP were used as nucleoside-triphosphate, though test results of these experiments are not indicated, an amount of formed triple-stranded DNA were not found to be above the detection level similar to using GTP.

However, according to another experiment (cf. a sixth embodiment which will be detailed later), a triple-stranded DNA is formed without ATP-γ S, though the formed amount of the triple-stranded DNA is very small. Thus, for forming a triple stranded-DNA, it is not able to conclude that nucleoside-triphosphate or its analog is essential. However, the DNA-protein complex forming process is desired to perform with a duly addition of nucleoside-triphosphate or its analog for ensuring the formation a stable triple-stranded-DNA.

Sixth Embodiment

Hereinafter a sixth embodiment of the present invention will be described such that explaining its portions similar to those of the above-described embodiments is made simplified or omitted.

Figure 9A:
FIG. 9 illustrates results of a triple-stranded-DNA-employed in a southern hybridization protocol (A) is an X-ray film photograph on which signals resulting from respective labeled oligonucleotide are recorded; and (B) is a photograph of a DNA-stained agarose gel after agarose gel electrophoresis.
Figure 9B:
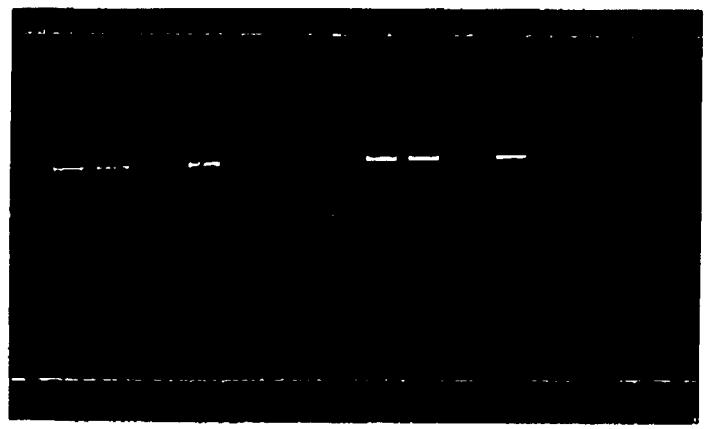

A comparative experiment whose results are indicated in FIG. 9 will be hereinbelow described.

Lane 2 indicates results of a reaction which was similar to the above-described reaction followed by lane 2 result of the second embodiment (cf.FIG. 5). In detail, in the DNA-protein complex forming process, a target. DNA(i.e. a linearized pUC118 DNA), a labeled probe DNA (i.e. a labeled oligonucleotide 3), and a RecA protein, and an Exonuclease I were brought into reaction with in a mixture of ATP-γ S, magnesium acetate, and tris-acetate. In brief, as a protein (i.e. enzyme), each of RecA protein and an Exonuclease I was added.

Lane 2 indicates a result of a reaction which was similar to the above-mentioned reaction followed by lane 2 result except that only RecA protein was added (i.e. Exonuclease I was not added) as enzyme in the DNA-protein complex forming process.

Lane 3 indicates a result of a reaction which was similar to the above-mentioned reaction followed by lane 2 result except that RecA protein, Exonuclease I, and Exonuclease VII were added as enzyme in the DNA-protein complex forming process.

Lane 4 indicates a result of a reaction which was similar to the above-mentioned reaction followed by lane 2 result except that only Exonuclease I was added as enzyme in the DNA-protein complex forming process.

Lane 5 indicates a result of a reaction which was similar to the above-mentioned reaction followed by lane 2 result except that Exonuclease I and Exonuclease VII were added as enzyme in the DNA-protein complex forming process.

Lane 6 indicates a result of a reaction which was similar to the above-mentioned reaction followed by lane 2 result except that only Exonuclease VII was added as enzyme in the DNA-protein complex forming process.

Lane 7 indicates a result of a reaction which was similar to the above-mentioned reaction followed by lane 2 result except that RecA protein and Exonuclease VII was added as enzyme in the DNA-protein complex forming press.

Lanes 8–14 indicates results of reactions which were similar to the reaction followed by lane 1–7 results of the present embodiment except that no ATP-γ S was added in the DNA-protein complex forming process.

As FIG. 9(A) indicates, signals are found on lanes 2,3, and 9, while on lanes 1, 4–8, and 10–14, signals are found.

Lane 1–7 results prove that as protein (enzyme) in the DNA-protein complex forming process at least RecA protein and Exonuclease I are essential. It is to be noted that the signal detected on lane 3 (in case of adding RecA protein, Exonuclease I, and Exonuclease VII) is found to be weaker in intensity than the signal detected on lane 2 (in case of adding RecA protein and Exonuclease I). This seems to result from a difficulty in forming a 3-chain forming region due to a portion of an end of one of the target and probe DNAs was cleaved by be Exonuclease VII. In other words, the existence of RecA protein blocks the proper activity of Exonuclease I to cleave an end of DNA. Whereas the existence of RecA protein is difficult to block the proper activity of Exonuclease VII to cleave an end of DNA, resulting in a difficulty in forming a 3chain forming region.

Lane 8–14 results prove that in the DNA-protein complex forming process even without ATP-γ S forming a stable triple-strained DNA is made possible so long as RecA protein and Exonuclease I are added as protein (enzyme). However, in light of weaker intensity of the signal detected on lane 9 (i.e. 1/50–1/100 of that of the signal detected on lane 2), forming a stable triple-stranded DNA seems to be established under an existence of ATP-γ S.

It is to be noted that despite of failing to detect a signal on lane 10 a very, very small or less-than-detection level amount of a triple-stranded is supposed to be formed on lane 10 in light of the signal detection on lane 3.

According to the above-description, it is conceivable that forming a stable triple-stranded DNA has to require as protein (enzyme) both RecA protein or it's analog and Exonuclease I or its analog. In addition, for establishing an effective formation of a stable triple-stranded DNA it is conceivable to add nucleoside-triphosphate (e g. ATP-γ S) or its analog forming in the DNA-protein complex process.

Seventh Embodiment

Hereinafter a seventh embodiment of the present invention will be described such that explaining its portions similar to those of the above-described embodiments is made simplified or omitted.

A comparative experiment whose results are indicated in FIG. 10 will be hereinbelow described Lane 1 indicates results of a reaction which was conducted without ATP-γ S and which was similar to the above-described reaction followed by lane 1 result of the second embodiment (cf.FIG. 5). In detail, in the DNA-protein complex forming process, a target DNA (i.e. a linearized pUC118 DNA), a labeled probe DNA (i.e. a labeled oligonucleotide 3: cf.FIG. 4), a RecA protein, and an Exonuclease I were brought into reaction with in a mixture of magnesium acetate and tris-acetate.

Lane 2 indicates a result of a reaction which was similar to the above-mentioned reaction followed by lane 2 result (cf.FIG. 5) of the second embodiment except that ATP-γ S was not added. In brief, the labeled probe DNA was a labeled oligonucleotide 4 (cf.FIG. 4).

Lane 3 indicates a result of a reaction which was similar to the above-mentioned reaction followed by lane 3 result (cf.FIG. 5) of the second embodiment except that no labeled oligonucleotide was added and the protein deactivation process was conducted. Thereafter, ethanol sedimentation was made to dissolve the DNA into an amount of SSC with a concentration of 1 time. The resulting solution is, after being added with 11 pmol of the labeled oligonucleotide 3, was held at a temperature of 60° C. for a time duration of 30 minutes. And, similar to the above-mentioned embodiments, a half amount of such a solution is made subject to agarose gel electrophoresis.

lane 4 indicates a result of a reaction which was similar to the reaction followed by lane 3 of the present invention except that labeled oligonucleotide 5 was use, as labeled probe DNA, instead of labeled oligonucleotide 3.

Lane 5 indicates a result of a reaction which was similar to the reaction followed by lane 3 of the present invention except that labeled oligonucleotide 4 was use, as labeled probe DNA, instead of labeled oligonucleotide 3.

Lane 6 indicates a result of a reaction which was similar to the reaction followed by lane 3 of the present invention except that labeled oligonucleotide 6 was use, as labeled probe DNA, instead of labeled oligonucleotide 3.

Lane 7 indicates a result of a reaction which was similar to the reaction followed by lane 3 of the present invention except that the DNA-protein complex forming process was performed without Exonuclease I. That is to say, labeled oligonucleotide 3 was used, as labeled probe DNA.

Lane 8 indicates a result of a reaction which was similar to the reaction followed by lane 5 of the present invention except that the DNA-protein complex forming process was performed without Exonuclease I. That is to say, labeled oligonucleotide 4 was used, as labeled probe DNA As FIG. 10(A) indicates,.apparently, no signals are detected on lanes 1–8. Lane 1 result and lane 2 result prove that a triple-stranded DNA can be formed rarely without ATP-γ S in the DNA-protein complex forming process.

Lane 3–6 results proves that it is impossible to form a stable triple-stranded DNA even an addition of probe DNA (i.e. oligonucleotide) after performing the protein deactivating process unless this probe DNA was added in the DNA-protein complex forming process. In addition, in the above-mentioned triple-stranded DNA, Exonuclease I made the end of the t DNA single-chain and the probe DNA was never bound to the target DNA.

Lane 7 and 8 results prove that it is impossible to form a stable triple-stranded even an addition of probe DNA (i.e. oligonucleotide) after performing the protein deactivating process unless this probe DNA and Exonuclease I were added in the DNA-protein complex forming process.

Thus, in accordance with the above description, it is convincible that for forming a stable triple-stranded DNA a temporal formation of a DNA-protein complex including a target DNA, a probe DNA, and a protein is required such that the probe DNA is added in the DNA-protein complex forming process.

Eight Embodiment

Hereinafter an eighth embodiment of the present invention will be described such that explaining its portions similar to those of the above-described embodiments is made simplified or omitted.

Figure 11:
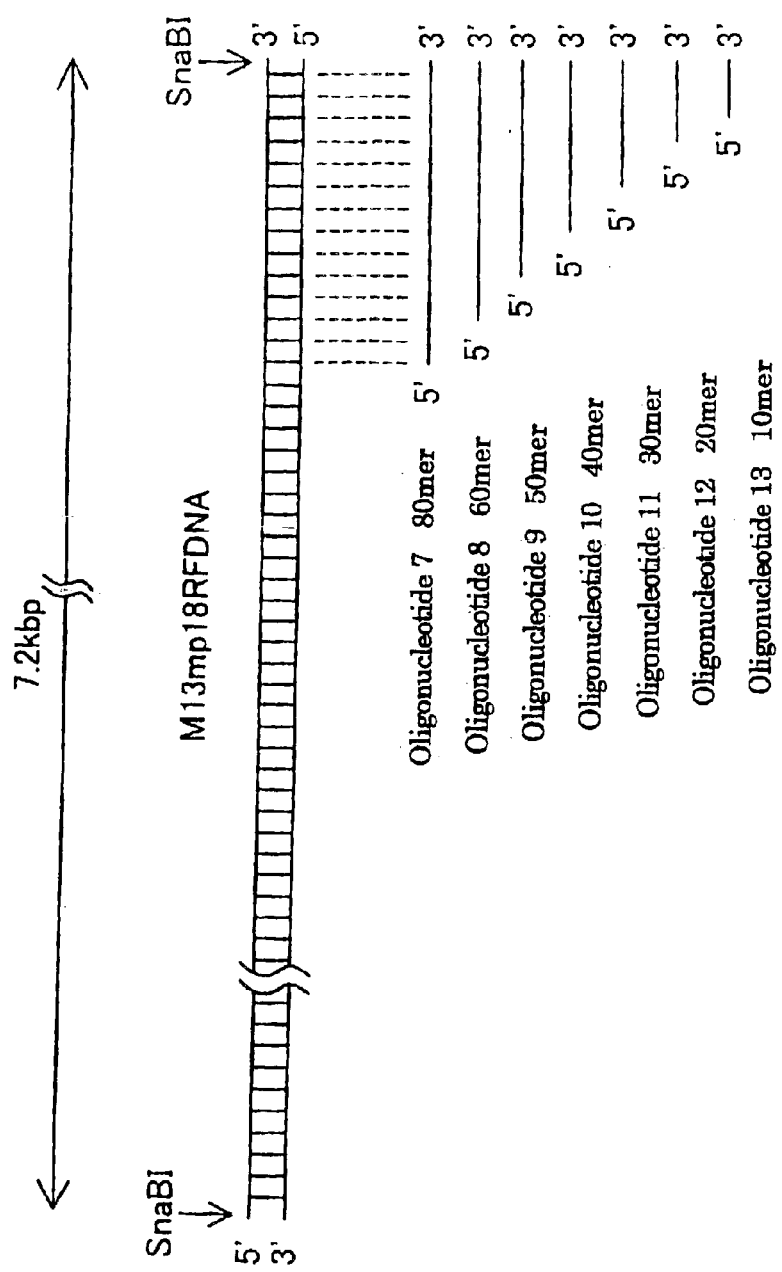
FIG. 11 illustrates how a DNA-protein complex and a triple-stranded DNA are formed in an eighth embodiment of the present invention.

A comparative experiment whose results are indicated in FIG. 12 will be hereinbelow described. First of all, as shown in FIG. 11, as a target DNA, a linearized double-stranded DNA was prepared which was obtained by cleaving a M13 mp 18 RF DNA (about 7.2 kb) with a restriction enzyme SnaB I. As to its basic sequence, cf. GeneBank Registration No.: X02513.

On the other hand, as a probe DNA, a single-stranded DNA (oligonucleotide 7[SEQ ID NO:7]) was prepared which is complementary to a vicinity region of one of ends of the above -mentioned target DNA (right-hand in the drawing). This oligonucleotide 7 included a base sequence which is 100% complementary to a base sequence of 80 mer which began at 5'-end of one of DNA chains (the lower placed DNA chain in the drawing).

In addition, a second probe DNA, a single-stranded DNA (oligonucleotide 8[SEQ ID NO: 8]) was prepared which was complementary to a vicinity region of one of ends of the above-mentioned target DNA (right-hand in the drawing). This oligonucleotide 8 included a base sequence which is 100% complementary to a base sequence of 60 mer which began at 5' end of one of DNA chains (the lower placed DNA chain in the drawing).

In addition, a third probe DNA, a single-stranded DNA (oligonucleotide 9[SEQ ID NO:9]) was prepared which was complementary to a vicinity region of one of ends of the above -mentioned target DNA (right-hand in the drawing). This oligonucleotide 9 included a base sequence which is 100% complementary to a base sequence of 50 mer which began at 5'-end of one of DNA chains (the lower placed DNA chain in the drawing).

In addition, a fourth probe DNA, a single-stranded DNA (oligonucleotide 9[SEQ ID NO:9]) was prepared which was complementary to a vicinity region of one of ends of the above-mentioned target DNA (right-hand in the drawing). This oligonucleotide 9 included a base sequence which is 100% complementary to a base sequence of 50 mer which began at 5'-end of one of DNA chains (the lower placed DNA chain in the drawing).

In addition, a fifth probe DNA, a single-stranded DNA (oligonucleotide 10[SEQ ID NO:10]) was prepared which was complementary to a vicinity region of one of ends of the above -mentioned target DNA (right-hand in the drawing). This oligonucleotide 10 included a base sequence which is 100% complementary to a base sequence of 40 mer which began at 5'-end of one of DNA chains (the lower placed DNA chain in the drawing).

In addition, a sixth probe DNA, a single-stranded DNA (oligonucleotide 11[SEQ ID NO:11]) was prepared which was complementary to a vicinity region of one of ends of the above mentioned target DNA (right-hand in the drawing). This oligonucleotide 10 included a base sequence which is 100% complementary to a base sequence of 30 mer which began at 5'-end of one of DNA chains (the lower placed DNA chain in the drawing).

In addition, a seventh probe DNA, a single-stranded DNA (oligonucleotide 12[SEQ ED NO:12]) was prepared which was complementary to a vicinity region of one of ends of the above-mentioned target DNA (right-hand in the drawing). This oligonucleotide 10 included a base sequence which is 100% complementary to a base sequence of 20 mer which began at 5'-end of one of DNA chains (the lower placed DNA chain in the drawing).

In addition, an eighth probe DNA, a single-stranded DNA (oligonucleotide 13[SEQ ID NO:13]) was prepared which was complementary to a vicinity region of one of ends of the above -mentioned target DNA (right-hand in the drawing). This oligonucleotide 10 included a base sequence which is 100% complementary to a base sequence of 10 mer which began at 5'-end of one of DNA chains (the lower placed DNA chain in the drawing).

5'-end of each of the oligonucleotide 7–13 was labeled with 32P with usage of T4 Polynucleotide Kinase and [γ-32P].

oligonucleotide 7:
  5'-acgagggtag caacggctac agaggctttg aggactaaag acttttcat gaggaagttt ccaaacg ggtaaaatac-3' (SEQ ID NO:7)

oligonucleotide 8:
  5'-agaggctttg aggactaaag acttttcat gal ccattaaacg ggtaaaatac-3' (SEQ ID NO:8)

oligonucleotide 9:
  5'-actaaag actttcat gaggaagttt ccataaacg ggtaaaatac3' (SEQ ID NO:9)

oligonucleotide 10:
  5'-acttttcat gaggaagttt ccattaaag ggaaatac3' (SEQ ID NO:10)

oligonucleotide 11:
  5'-gaggaagttt ccattaaacg ggtaaaatac-3' (SEQ ID NO:11)

oligonucleotide 12:
  5'-ccattaaacg ggtaaaatac-3' (SEQ ID NO:12)

oligonucleotide 13:
  5'-ggtaaaata-3' (SEQ ID NO:13)

Next, in the DNA-protein complex forming process, 200 ng of the target DNA (i.e. the linearized M13 mp 18 RF DNA), 1 pmol of the labeled oligonucleotide 7, and 4-unit Exonuclease I were held at a temperature of 37° C. for 30 minutes in a mix of 4.8 mM of ATP-γ S, 30 mM of magnesium acetate e, and 30 mM of tris-acetate (pH: 72).

Thereby, similar to the above-described First Embodiment, a DNA-protein complex was formed or produced. In detail, the stable DNA-protein complex was formed or produced such that the vicinity region of the end (right-hand in FIG. 11) of on the target DNAs was bound with the whole of the oligonucleotide 7 at least with the RecA protein (cf.FIG. 2).

In the subsequent protein deactivating process, the resulting reaction solution was added with 0.5%(W/Vol) SDS and 0.7 mg/ml proteinase K to hold at a temperature of 37° C. for 30 minutes, thereby deactivating the Rec A and the Exonuclease I.

Thereby, like the above-described First Embodiment, a stable triple-stranded DNA was formed. In detail, a stable triple-stranded DNA was formed which had a 3-chain forming region formed by binding the whole of the oligonucleotide 7 to the vicinity region of the end (right-hand in FIG. 11) of one of the target DNAs (cf.FIG. 2). This triple-stranded DNA requires no specially prepared protein etc to maintain its structure and the s can remain unchanged even more or less heat is applied thereto.

Next similar to the above-described First Embodiment, in the electrophoresis process, a half amount of the reaction solution was brought into 1% agarose gel electrophoresis The resulting agarose gel electrophoresis was immersed in a solution of ethidium bromide to stain the DNA in the agarose gel therewith. Thereafter, t a picture was taken to record the DNA The result appears on lane 1 in FIG. 12 (B).

Thereafter, similar to the foregoing First Embodiment, in the detection process after the dry process, an autoradiogram of the dried agarose gel was taken to record signals on an X-ray film which resulted from the labeled oligonucleotide 3. The results appear on lane 1 in FIG. 12 (A).

Figure 12B:
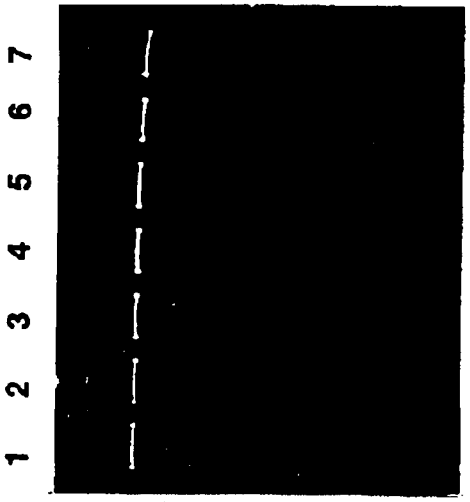
FIG. 12 illustrates photographs as alternatives of respective drawings which indicate results of a triple-stranded-DNA-employed southern hybridization in the eighth embodiment of the present invention, wherein (A) is an X-ray film photograph on which are recorded signals resulting from respective labeled oligonucleotide and (B) is a photograph of a DNA-stained agarose gel after agarose gel electrophoresis.
Figure 12A:
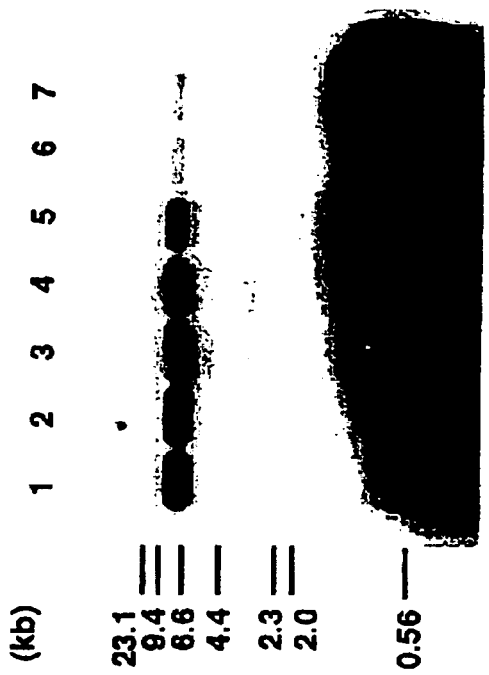

In FIGS. 12(A) and 12(B), the detected signals which appear near about 7.2 kbp resulted from the triple-stranded DNA in which the oligonucleotide 7 is bound to the target DNA.

Such a Southern hybridization, which is similar to that in the above-explained First Embodiment, when compared to the conventional Southern makes it possible to eliminate skilled and/or operations such as a transfer of the DNA in the agarose gel to a membrane, an immersion of this membrane in an probe DNA solution, and washing the membrane. Thus, conducting or doing Southern hybridization can be established easily and in a shorter time duration.

Lane 2 indicates a result of a reaction which was similar to the reaction followed by lane 1 of the present invention except that in the DNA-protein forming process as the probe DNA, the labeled oligonucleotide 8 was added Lane 3 indicates a result of a reaction which was similar to the reaction followed by lane 1 of the present invention except that in the DNA-protein forming process as the probe DNA, the labeled oligonucleotide 9 was added.

Lane 4 indicates a result of a reaction which was similar to the reaction followed by lane 1 of the present invention except that in the DNA-protein forming process as the probe DNA, the labeled oligonucleotide 10 was added.

Lane 5 indicates a result of a reaction which was similar to the reaction followed by lane 1 of the present invention except that in the DNA-protein forming process as the probe DNA, the labeled oligonucleotide 11 was added.

Lane 6 indicates a result of a reaction which was similar to the reaction followed by lane 1 of the present invention except that in the DNA-protein forming process as the probe DNA, the labeled oligonucleotide 12 was added.

Lane 7 indicates a result of a reaction which was similar to the reaction followed by lane 1 of the present invention except that in the DNA-protein forming process as the probe DNA, the labeled oligonucleotide 13 was added As FIG. 12(A) indicates apparently signals are found on all lanes 1–7. The signals on lanes 1–4 are stronger intensity, while the signals on lanes 5–7 are found to be weaker and weaker as lane number proceeds. These results prove that forming a stable triple-stranded DNA becomes easier and easier as the probe DNA (i.e. the oligonucleotide) becomes longer and longer. It is believed that ensuring a sufficient amount of the formed stable triple-stranded DNA requires, in addition to a sufficient reaction time duration of the DNA-protein complex forming process, a sufficient length of the probe DNA (i.e. the oligonucleotide) which is not less than 20 mer, preferably not less than 30 mer.

Ninth Embodiment

Figure 13:
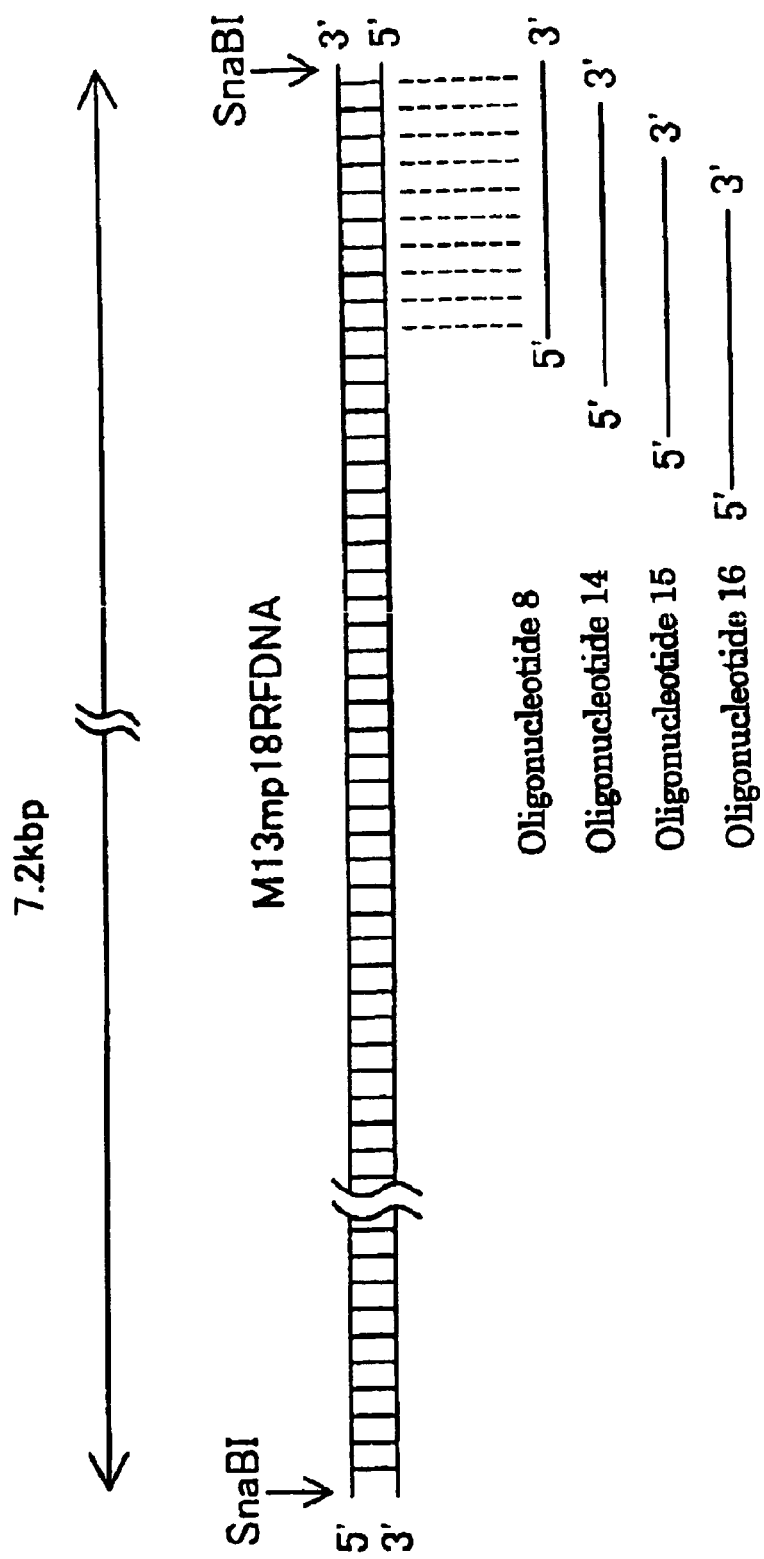
FIG. 13 illustrates the formation of a DNA-protein complex and a triple-stranded DNA.
Figure 14A:
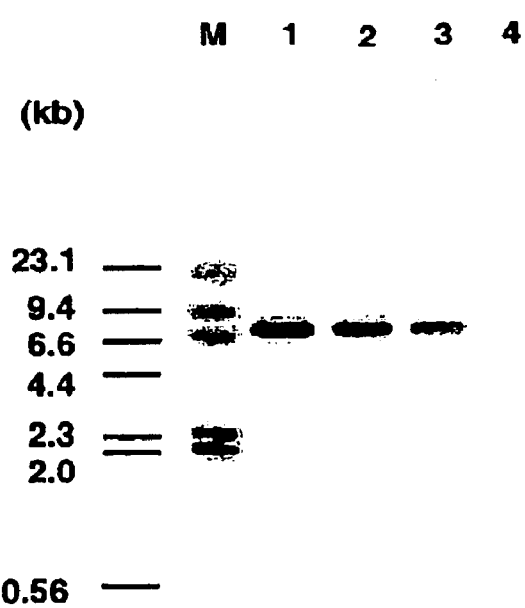
FIG. 14 illustrates results of a triple-stranded-DNA-employed in a southern hybridization protocol (A) is an X-ray film, photograph on which signals resulting from respective labeled oligonucleotide are recorded; and (B) is a photograph of a DNA-stained agarose gel after agarose gel electrophoresis.
Figure 14B:

Hereinafter a ninth embodiment of the present invention will be described such that explaining its portions similar to those of the above-described embodiments is made simplified or omitted A comparative experiment whose results are indicated in FIG. 14 will be hereinbelow described. First of all, as shown in FIG. 13, similar to the above-described Eighth Embodiment, as target DNAs, linearized double-stranded DNAs were prepared which were obtained by cleaving a M13 mp 18 RF DNA (about 7.2 kbp) with a restriction enzyme SnaB I.

On the other hand, as a probe DNA, a single-stranded DNA (oligonucleotide 8[SEQ ID NO:8]) was prepared in the above-described Eighth Embodiment.

In addition, as a second probe DNA, an oligonucleotide 14([SEQ ID NO:14]) of 60 mer was prepared which included a base sequence which is 100% complementary to a base sequence of 60 mer which began at the eleventh base sequence from the 5'-end of one of DNA chains (the lower placed DNA chain in the drawing).

In addition, as a third probe DNA, an oligonucleotide 15([SEQ ID NO:15]) of 60 mer was prepared which included a base sequence which is 100% complementary to a base sequence of 60 mer which began at the twenty-first base sequence from the 5'-end of one of DNA chains (the lower placed DNA chain in the drawing).

In addition, as a fourth probe DNA, an oligonucleotide 16([SEQ ID NO:16]) of 60 mer was prepared which included a base sequence which is 100% complementary to a base sequence of 60 mer which began at the thirty-first base sequence from the 5'-end of one of DNA chains (the lower placed DNA chain in the drawing).

5'-end of each of the oligonucleotide 8 and 14–16 was labeled with 32P with T4 Polynucleotide Kinase and [γ-32P].

oligonucleotide 14:
5'-caacggctac agaggctttg aggactaaag acttttcat gttt ccaaaacg-3' (SEQ ID NO:14)

oligonucleotide 15:
5'-acgagggtag caacggctac agaggctttg aggactaaag acttttcat gaggaagttt-3' (SEQ ID NO:15)

oligonucleotide 16:
5'-cagcatcgga acgagggtag caacggctac agaggctttg aggac-taaag acttttcat-3' (SEQ ID NO:16)

In FIG. 14, lane M is, similar to that of each of the foregoing Embodiments, a DNA size marker.

Lane 1 indicates a result of a reaction which was similar to the reaction followed by lane 2 result (cf.FIG. 12) of the above-described Eighth Embodiment. That is, in the DNA-protein forming process as the target DNA and the probe DNA the linearize M13mp18 RF DNA and the labeled oligonucleotide 8 were, respectively, used.

Lane 2 indicates a result of a reaction which was similar to the reaction followed by lane 1 result of the present embodiment except that in the DNA-protein forming p as the probe DNA, the labeled oligonucleotide 14 was added.

Lane 3 indicates a result of a reaction which was similar to the reaction followed by lane 1 result of the present embodiment except that in the DNA-protein forming process as the probe DNA, the labeled oligonucleotide 15 was added.

Lane 4 indicates a result of a reaction which was similar to the reaction followed by lane 1 result of the present embodiment except that in the DNA-protein forming process as the probe DNA, the labeled oligonucleotide 16 was added.

As FIG. 14(A) indicates apparently signals are found on lanes 1–3 but no signal is found on lane 4. Of the found signals, the signal on lane 1 is the strongest in intensity, while the signal on lane 3 is the weakest This proves that a formed triple-stranded DNA can be made most stable unless a 2-chain forming region exists (in case of lane 1) on an extension of the 3'-end of the probe DNA constituting the 3-chain forming region during formation of the triple-stranded DNA. In addition, even if a 2-chain forming region exists on an extension of the 3'-end of the probe DNA constituting the 3-chain forming region during formation of the triple-stranded DNA, the formed triple-stranded DNA can be stable subject to that the 2-chain forming region is as short as less than about 20 bp (in case of lane 2 or 3). On the other hand, it is proved that a formed triple-stranded DNA cannot be made stable if a long 2-chain forming region exists (in case of lane 4) on an extension of the 3'-end of the probe DNA constituting the 3-chain forming region during formation of the triple-stranded DNA.

The reason of such results may be that an existence of 2-chain forming region which exists on an extension of the 3'-end of the probe DNA constituting the 3-chain forming region causes a structural stress, resulting in an easy deletion of the 3-chain forming region. Thus, for forming a stable triple-stranded DNA, it is preferable that the 2-chain forming region should be as short as possible or at least not greater than about 20 bp which is formed on an extension of the 3'-end of the probe DNA constituting the 3-chain forming region when the triple-stranded DNA is formed. The most preferable method is to exclude the formation of the 2-chain forming region.

Tenth Embodiment

Hereinafter a tenth embodiment of the present invention will be described such that explaining its portions similar to those of the above-described embodiments are made simplified or omitted.

Figure 15A:
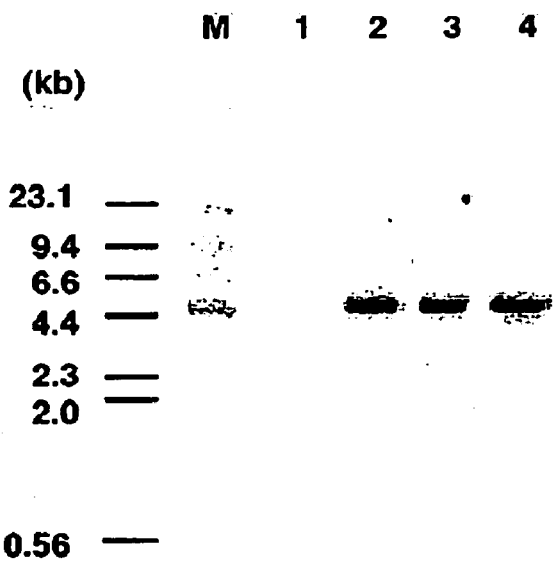
FIG. 15 illustrates results of a triple-stranded-DNA-employed in a southern hybridization protocol (A) is an X-ray film photograph on which signals resulting from respective labeled oligonucleotide are recorded; and (B) is a photograph of a DNA-stained agarose gel after agarose gel electrophoresis.
Figure 15B:

A comparative experiment whose results are indicated in FIG. 15 will be hereinbelow described Lane M is, similar to that of each of the foregoing Embodiments, a DNA size marker.

Lane 1 indicates a result of a reaction which was similar to the reaction followed by lane 1 result (cf.FIG. 5) of the above-described Second Embodiment except that in the DNA-protein complex forming process no magnesium acetate was added.

Lane 2 indicates a result of a reaction which was similar to the reaction followed by lane 1 result (cf.FIG. 5) of the above-described Second Embodiment such that in the DNA-protein complex forming process an amount of magnesium acetate was 20 mM.

Lane 3 indicates a result of a reaction which was similar to the reaction followed by lane 2 result of the present embodiment except that in the DNA-protein complex forming process an amount of magnesium acetate was 40 mM.

Lane 4 indicates a result of a reaction which was similar to the reaction followed by lane 2 result of the present embodiment except that in the DNA-protein complex forming process an amount of magnesium acetate was 60 mM.

As FIG. 15(A) indicates apparently signals are detected on lanes 2–4 but no signal is found on lane 1. The signals on lanes 2–4 are of same intensity. According to such results, it seems to require magnesium acetate such as Mg ion or its analog in the DNA-protein complex forming process if a stable triple-stranded DNA is desired to form by using at least RecA protein and Exonuclease I. In such a case, the sufficient amount of the amount magnesium acetate is thought to be about 20 mM.

Eleventh Embodiment

Hereinafter an eleventh embodiment of the present invention will be described such that explaining its portions similar to those of the above-described embodiments are made simplified or omitted.

Figure 16A:
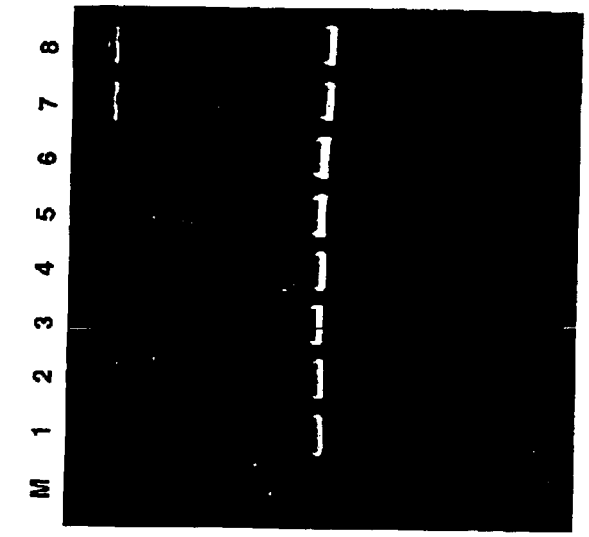
FIG. 16 illustrates results of a triple-stranded-DNA-employed in a southern hybridization protocol (A) is an X-ray film photograph on which signals resulting from respective labeled oligonucleotide are recorded; and (B) is a photograph of a DNA-stained agarose gel after agarose gel electrophoresis.
Figure 16B:
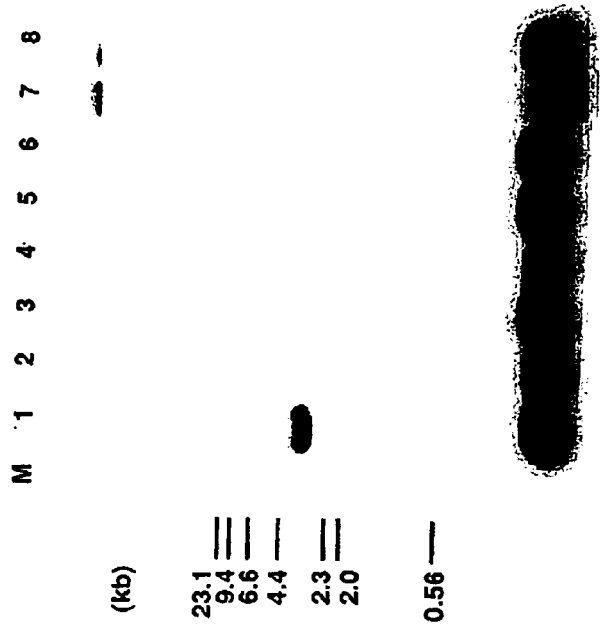

A comparative experiment whose results are indicated in FIG. 16 will be hereinbelow described.

Lane M is, similar to that of each of the foregoing Embodiments, a DNA size marker.

Lane 1 indicates a result of a reaction which was similar to the reaction followed by lane 1 result (cf.FIG. 5) of the above-described Second Embodiment. That is, in the DNA-protein complex forming process 20 mM of magnesium acetate was added into the reaction solution.

Lane 2 indicates a result of a reaction which was similar to the reaction followed by lane 1 result of the present embodiment except that in the DNA-protein complex forming process instead of magnesium acetate 10 mM of cobalt chloride was added in the reaction solution.

Lane 3 indicates a result of a reaction which was similar to the reaction followed by lane 1 result of the present embodiment except that in the DNA-protein complex forming process in addition to the magnesium acetate 10 mM of cobalt chloride was added in the reaction solution.

Lane 4 indicates a result of a reaction which was similar to the reaction followed by lane 1 result of the present embodiment except that in the DNA-protein complex forming process no magnesium acetate was added in the reaction solution.

Lane 5 indicates a result of a reaction which was similar to the reaction followed by lane 1 result of the present embodiment except that in the DNA-protein complex forming process a target DNA (pUC118 DNA), a labeled oligonucleotide 3, a RecA protein, and an Exonuclease I are brought into reaction in a mixture of 4.8 mM of ATP-γ S. 10 mM of magnesium acetate, 66 mM of calcium acetate, 33 mM of tris-acetate (pH: 7.8), and 0.5 mM of DTT.

Lane 6 indicates a result of a reaction which was similar to the reaction followed by lane 5 result of the present embodiment except that in the DNA-protein complex forming process 10 mM of cobalt chloride was further added Lane 7 indicates a result of a reaction which was similar to the reaction followed by lane 5 result of the present embodiment except that in the DNA-protein complex forming process 4.8 mM of GTP was used instead of the ATP-γ S.

Lane 8 indicates a result of a reaction which was similar to the reaction followed by lane 5 result of the present embodiment except that in the DNA-protein complex forming process 4.8 mM of ATP was used instead of the ATP-γ S.

As FIG. 16(A) indicates apparently a signal is detected on only lane 1 and no signal are found on other lanes. Lane 1 and 4 results prove that magnesium acetate is required in the DNA-protein complex forming process if a stable triple-stranded DNA is desired to form by using at least RecA protein and Exonuclease I. In addition the lane 2 result proves that Co ion fails to substitute Mg ion. The lanes 3,5, and 6 results prove that even if an Mg ion exists existences of respective Ca and Co ions make it impossible to for a stable triple-stranded DNA. Lane 7 and 8 results prove that effective formation of a stable triple-stranded DNA is impossible to attain even if ATP or GTP is used instead of ATP-γ S. In view of these deduction facts, it can be thought that for effective formation of a stable triple-stranded DNA an Mg ion is essential in the DNA-protein complex forming process if at least RecA protein and Exonuclease I are used.

Twelfth Embodiment

Hereinafter a twelfth embodiment of the present invention will be described such that explaining its portions similar to those of the above-described embodiments is made simplified or omitted.

Figure 17:
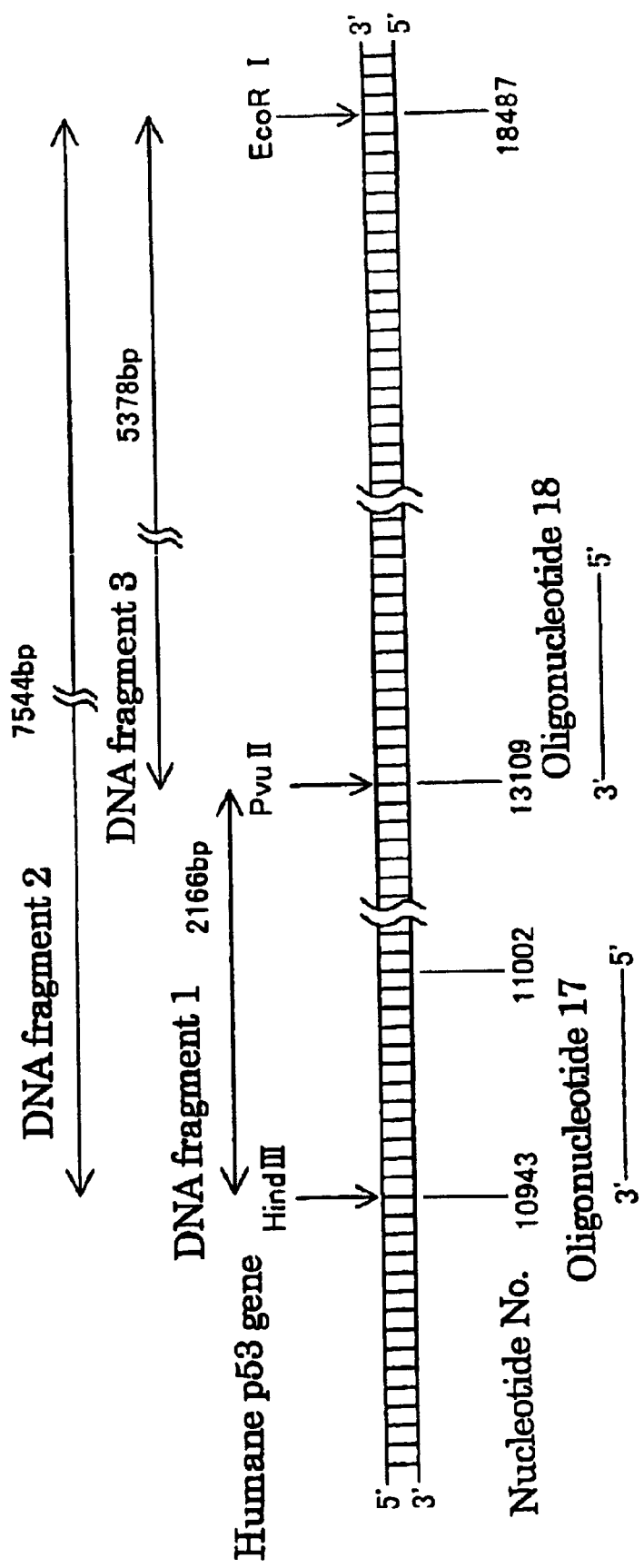
FIG. 17 illustrates the formation of a DNA-protein complex and a triple-stranded DNA.

As shown in FIG. 17, as target DNAs, linearized double-stranded DNAs were prepared which were obtained by cleaving a human genome DNA by restriction enzymes Hind III and Pvu II. In this target DNA, a p53-gene-encoded DNA fragment 1 (about 2.2 kbp) was included. In addition, as second target DNAs, linearized double-stranded DNAs were prepared which were obtained by cleaving a human genome DNA by restriction enzymes Hind III and EcoR I. In this target DNA, a p53-gene-encoded DNA fragment 2 (about 7.5 kbp) was included. Moreover, as third target DNAs, linearized double-stranded DNAs were prepared which were obtained by cleaving a human genome DNA by restriction enzymes Pvu II and EcoR I. In this target DNA, a p53-gene-encoded DNA fragment 3 (about 5.4 kbp) was included. It is to be noted that the base sequence of the above-mentioned human p53 gene should be referred to GeneBank Access No.:U94788.

On the other hand, a single-stranded DNA (i.e. an oligonucleotide 17[SEQ ID NO:17]) was prepared which was complementary to a vicinity end region at a side of the Hind III cleavage site of each of the DNA fragments I and 2. In detail, the prepared oligonucleotide 17 included a base sequence of 60 mer which was complementary to a 60 mer base sequence which begun at 5'-end of the side of the Hind III cleavage site of one of the DNA fragments 1 and 2.

In addition, as another probe DNA, a single-stranded DNA (i.e. an oligonucleotide 18[SEQ ID NO: 18]) was prepared which was complementary to a vicinity end region at a side of the EcoR I cleavage site of each of the DNA fragments 2 and 3. In detail, the prepared oligonucleotide 18 included a base sequence of 60 mer which was complementary to a 60 mer base sequence which begun at 5'-end of the side of the EcoR I cleavage site of one of the DNA fragments 2 and 3. Then, the 5'-end of each of the oligonucleotide 17 and 18 was labeled with 32P with T4 Polynucleotide Kinase and [γ-32P].

Oligonucleotide 17:

5'-ctttg cagtgaaagg aatcaaagaa atggagccgt gtatcaggtg gggaagggtg ggggc-3' (SEQ ID NO:17)

Oligonucleotide 18:

5'-ctgtgggot gattccacac ccccgccgg cacccgcgtc cgcgcatgg ccatctacaa g-3' (SEQ ID NO:18) Next, in the DNA-protein complex forming process, 5 μg of the target DNA which was obtained by cleaving the human genome DNA by the restriction enzymes Hind III and Pvu II and which included the above-mentioned DNA fragment 1, 5 pmol of the labeled oligonucleotide 17, 10 μg of a RecA protein and 4-unit Exonuclease I were held at a temperature of 37° C. for 30 minutes in a mixture of 4.8 mM of the ATP-γ S, 20 mM of the magnesium acetate, and 30 mM of the tris-acetate (pH:7.2).

Thus, similar to the foregoing First Embodiment, a DNA-protein complex was formed. That is to say, the whole of the oligonucleotide 17 was bound to the end of the Hind III cleavage site of the above-mentioned DNA fragment 1 included in the target DNA to form the stable DNA-protein complex such that at least the RecA protein involved in the formation (cf.FIG. 2).

Next, in the protein deactivating process, the reaction solution was added with 0.5% (W/Vol) SDS and 0.7 mg/ml proteinase K and the resultant mixture was held at a temperature of 37° C. for 30 minutes to deactivate the RecA protein and the Exonuclease I.

Thus, similar to the foregoing First Embodiment, a stable triple-stranded DNA was formed. That is to say, the triple-stranded DNA was formed which had a 3-chain forming region obtained by binding the whole of the oligonucleotide 17 to the end of the Hind III cleavage site of the above-mentioned DNA fragment 1 included in the target DNA (cf.FIG. 2). The obtained triple-stranded DNA was free from a specially prepared protein to maintain its stricture and its structure can rain unchanged even if a heat is applied thereto more or less.

Thereafter, as to the resultant reaction solution, one-time phenol/chloroform extraction and subsequent twice filtering using S-400 spin column (Amersham Pharmacia Biotech Corporation/USA) were performed to eliminate or delete the labeled oligonucleotide 17 which had not been reacted.

Next, the whole amount (about 20 μ litters) of the resultant reaction solution was subjected to 1%-agarose gel electrophoresis. Then, the agarose gel was immersed into an ethidium bromide solution to stain the DNA in the agarose gel and the stained DNA was recorded by taking a picture. The result is indicated on lane 1 in FIG. 18(B).

Figure 18A:
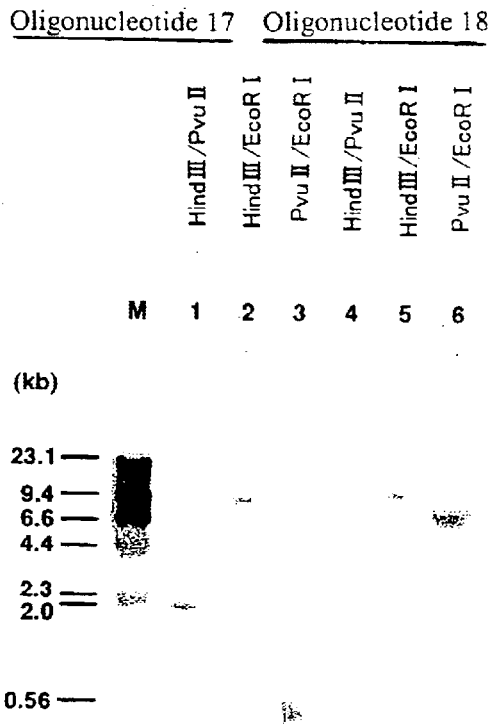
FIG. 18 illustrates results of a triple-stranded-DNA-employed in a southern hybridization protocol (A) is an X-ray film photograph on which signals resulting from receptive labeled oligonucleotide are recorded; and (B) is a photograph of a DNA-stained agarose gel after agarose gel electrophoresis.
Figure 18B:
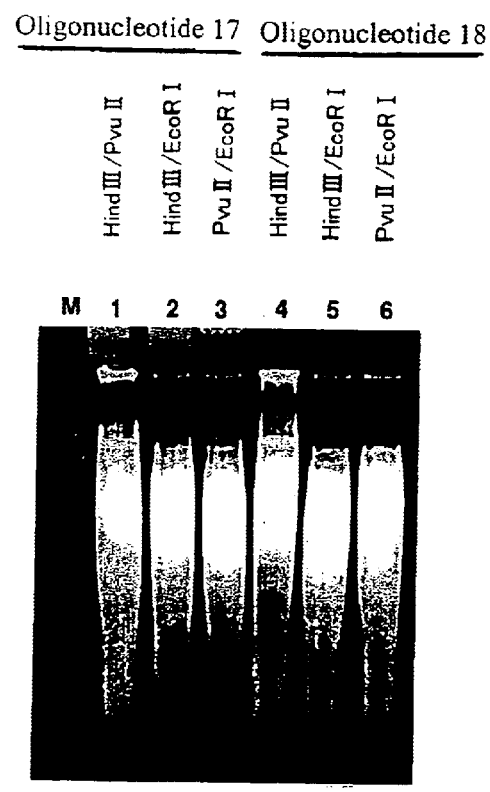
Figure 19:
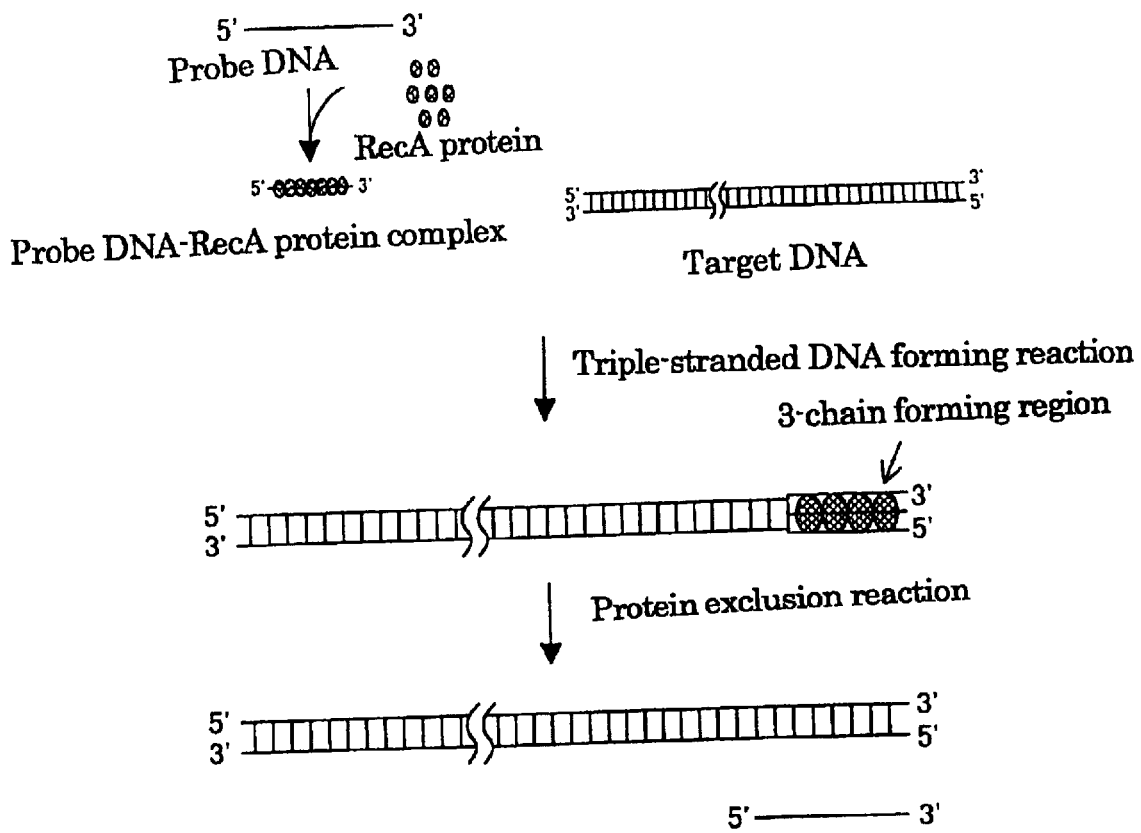
FIG. 19 illustrates forming a triple-stranded DNA and disassociated with methods conventionally used in the art.

Next, the above-mentioned agarose gel was placed on a filter paper to dry with a gel-drying device. Thereafter, the agarose gel was taken with an autoradiogram to record a signal resulted from the labeled oligonucleotide 17 on an X-ray film. The result is shown on lane 1 in FIG. 18 (A). In FIG. 18 (A), the signal found at a portion near about 2.2 kbp results from the triple-stranded DNA formed by binding the oligonucleotide 17 to the DNA fragment 1. It is to be noted that such a genomic Southern hybridization which is due to similarly to the foregoing process are followed by few skilled operation and/or long-time required operation, resulting in short time and easy operation.

At this stage, a comparative experiment whose results are indicated in FIG. 18 will be hereinbelow described.

Lane M is, similar to that in the foregoing embodiments, a DNA size marker.

Lane 2 indicates a result of a reaction which was similar to the reaction followed by lane 1 of the present embodiment except that in the DNA-protein complex forming process 5 μg of the target DNA was used which included the DNA fragment 2 and which was obtained by cleaving the human genome DNA with the restriction enzymes Hind III and EcoR I.

Lane 3 indicates a result of a reaction which was similar to the reaction followed by lane 1 of the present embodiment except that in the DNA-protein complex forming process 5 μg of the target DNA was used which included the DNA fragment 3 and which was obtained by cleaving the human genome DNA with the restriction enzymes Hind III and Pvu II.

Lane 4 indicates a result of a reaction which was similar to the reaction followed by lane 1 of the present embodiment except that in the DNA-protein complex forming process as the probe DNA the labeled oligonucleotide 18 was added and as the target DNA one was used which was obtained by cleaving the human genome DNA with the restriction enzymes Hind II and Pvu II.

Lane 5 indicates a result of a reaction which was similar to the reaction followed by lane 2 of the present embodiment except that in the DNA-protein complex forming process as the target DNA one was used which was obtained by cleaving the human genome DNA with the restriction enzymes Hind III and EcoR I.

Lane 6 indicates a result of a reaction which was similar to the reaction followed by lane 3 of the present embodiment except that in the DNA-protein complex forming process as the target DNA one was used which was obtained by cleaving the human genome DNA with the restriction enzymes Pvu II and EcoR I.

As apparent from FIG. 18 (A) signals are detected on lanes 1, 2, 5, and 6, while no signal are detected on lanes 3 and 4.

Lane 1, 2, 5, and 6 results prove, similar to lane 1 result as mentioned above, proves that a stable triple-stranded DNA is formed. The signal detected at a portion near about 7.5 kbp on lane 2 results from the triple-stranded DNA formed by the chemical bond between the DNA fragment 2 and the oligonucleotide 17. The signal detected at a portion near about 7.5 kbp on lane 5 results from the triple-stranded DNA formed by the chemical bond between the DNA fragment 2 and the oligonucleotide 18. The signal detected at a portion near about 5.4 kbp on lane 6 results from the triple-stranded DNA formed by the chemical bond between the DNA fragment 3 and the oligonucleotide 18.

On the other hand, lane 3 and 4 results prove that forming a stable triple-stranded DNA can not be attained due to a deletion of the 3-chain forming region when a long 2-chain forming region on an extension of the 3'-end of the oligonucleotide constituting the 3-chain forming region. This seems to be due to the fact that a structure stress caused by the long 2-chain forming region extinguishes the 3-chain forming region.

According to the above-description, even in genomic Southern hybridization, utilizing triple-stranded DNA seems to be effective. In addition, for forming a stable triple-stranded, it seems to require that a long 2-chain forming region should be prevented on an extension of the 3'-end of the oligonucleotide constituting the 3-chain forming region.

[Modifications]

It is to be noted that the present invention is not restricted to above-described embodiments which are described in great detail. That is to say, the foregoing embodiments are for purposes of illusion and not limitation. Needless to say, numerous modifications can be made possible without departing from the gist of the present invention. Some of the exemplified modifications will be described hereafter.

Instead of the oligonucleotide, as the probe DNA (single-stranded DNA) in each of the foregoing embodiments, which is 100% complementary to a portion of the target DNA (double-stranded DNA), a probe DNA is available which is of a substantial complementary (i.e. above 70–80%) to form a stable triple-stranded DNA. Also, a probe DNA (single-stranded DNA) can be of, in addition to the region which is complementary to the double-stranded DNA, another base sequence which is not complementary to the double-stranded DNA The reason is such a probe DNA can be bound to the target DNA to for a triple-stranded DNA However, for making such a triple-stranded DNA stable, the whole of the probe DNA (single-stranded DNA) is preferred to be 100% complementary to a portion of the target DNA (double-stranded DNA) as indicated in each of the foregoing embodiments. In addition, the probe DNA is not necessary to result from an artificial synthesized oligonucleotide. The origin of the probe DNA is not of concern. The reason is that even though a substance other than oligonucleotide is used as the probe DNA forming a stable triple-stranded can be attained.

Instead of RecA protein used in each of the foregoing embodiments, as the recombinant protein, another substance is available. However, in fight of availability, safety, and function, RecA protein seems to be best Instead of Exonuclease I, as the nuclease for forming the triple-stranded DNA in each of the foregoing embodiments, another protein is available which is similar to Exonuclease I in function, as previously mentioned. However, in light of availability, safety, and function, Exonuclease I seems to be best Instead of a set of SDS and proteinase K which is used for deactivating the protein in the protein deactivating process in each of the foregoing embodiments, chelate compound such as ethylenediaminetetraacetic acid is available. The reason is that such a substance has a function of deactivating protein.

Instead of forming the 3-chain forming region in each of the foregoing e i ts such that the probe DNA (single-stranded DNA) is bound to the vicinity of end portion of one of the target DNAs (double-stranded DNAs), forming 3-chain forming regions can be employed such that the probe DNA (single-stranded DNA) is bound to the vicinity of end portion of each of the target DNAs (double-stranded DNAs). Thus-obtained triple-stranded DNAs can remain its structure even without specially prepared protein etc.

The present application is based on and claims priority under 35 U.S.C §119 to Japanese Patent Application No. 2001-81527 filed on Mar. 21, 2001, the entire content of which is incorporated herein by reference.

The invention has thus been shown and description with reference to specific embodiments however, it should be understood that the invention is n no way limited to the details of the illustrated structures but changes and modifications may be made without departing from the scope of the appended claims.

What is claimed is:

1. A method of preparing a triple-stranded DNA molecule comprising
   a. forming a DNA and protein complex, wherein the DNA comprises a linear double-stranded DNA and a linear single-stranded DNA which is complementary to a 5' end region of one strand in the linear double stranded DNA; and wherein the protein comprises a RecA protein and an exonuclease; and
   b. preparing a DNA molecule comprising triple stranded parts by deactivating and removing the protein from the complex.

2. The method according to claim 1, wherein the region that is complementary between a 5' end of one strand of the double-stranded DNA molecule and the single-stranded DNA comprises at least 20 nucleotides.

3. The method according to claim 1, wherein the RecA protein is obtained from *Escherichia coli, Thermus thermophilus, Agrobacterium tumefaciens, Bacillus subtilis, Methylophilus methylotrophus, Vibrio cholerae,* or *Ustilago maydis.*

4. The method according to claim 1, wherein the exonuclease is *Escherichia coli* Exonuclease I.

5. The method according to claim 1, wherein the forming a DNA and protein complex is conducted in the presence of a nucleotide triphosphate.

6. The method according to claim 1, wherein the molar ratio of the single stranded DNA relative to the double-stranded DNA is from 1 to 100.

7. The method according to claim 1, wherein removing the protein from the complex comprises adding a solution of one or more of a chelating agent and a starch degrading enzyme.

8. The method according to claim 7, wherein the chelating agent is ethylenediaminetetraacetic acid.

9. The method according to claim 7, wherein the starch degrading enzyme is proteinase K.

10. The method according to claim 1, wherein the single-stranded DNA comprises a detectable-label.

* * * * *